United States Patent
Salles

(10) Patent No.: US 6,331,315 B1
(45) Date of Patent: *Dec. 18, 2001

(54) POWDER COMPOSITIONS OF UNILAMELLAR LIPOSOMES

(75) Inventor: Jean-Pierre Salles, Eguilles (FR)

(73) Assignee: Lipogel, Allauch (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/445,441

(22) PCT Filed: Jun. 11, 1998

(86) PCT No.: PCT/FR98/01203

§ 371 Date: Feb. 16, 2000

§ 102(e) Date: Feb. 16, 2000

(87) PCT Pub. No.: WO98/56351

PCT Pub. Date: Dec. 17, 1998

(30) Foreign Application Priority Data

Jun. 11, 1997 (FR) .................................. 97 07254

(51) Int. Cl.$^7$ ........................... A61K 9/127; A61K 9/133

(52) U.S. Cl. ........................... 424/450; 424/489; 424/490; 424/499; 428/402.2; 514/824

(58) Field of Search ................. 424/450, 489–502, 424/484, 1.21, 9.321, 9.51; 428/402.2; 264/4.1, 4.3, 4.6; 514/824

(56) References Cited

U.S. PATENT DOCUMENTS

| | | | |
|---|---|---|---|
| 5,626,870 | * | 5/1997 | Monshipouri .................. 424/450 |
| 5,783,211 | * | 7/1998 | Manzo ........................... 424/450 |
| 5,945,120 | * | 8/1999 | Hauton .......................... 424/450 |

FOREIGN PATENT DOCUMENTS

| | | |
|---|---|---|
| 38 15 473 A | 11/1989 | (DE) . |
| 297 04 822 U | 5/1997 | (DE) . |

(List continued on next page.)

OTHER PUBLICATIONS

Williams in Perspedives in Bid Med. 27, 3, p. 417 1984.*
BNA's Intellectual Property Library on CD—Full Text of Cases (USPQ First Series); In re Oda, Fujii, Moriga, and Higaki, 170 USPQ 268 (CCPA 1971); pp. 1–11.
J. Microencapsulation, 1995, vol. 12, No. 3; "Factors affecting microencapsulation of drugs in Liposomes"; S. B. Kulkarni, et al.; pp. 229–237.

Primary Examiner—Gollamudi S. Kishore
(74) Attorney, Agent, or Firm—Oblon, Spivak, McClelland, Maier & Neustadt, P.C.

(57) ABSTRACT

The invention concerns powder compositions of stabilised unilamellar liposomes, comprising at least an external lipid phase and a internal aqueous polar nucleus gelled at room temperature, the method for preparing them and their applications as nutritional additives and in pharmaceutical compositions to be orally administered (with action against lipemia). Said compositions essentially consist of unilamellar liposomes comprising an external lipid phase consisting of class 4 lipids (phospholipids) and an internal aqueous nucleus consisting essentially of a mixture M of at least two different non-polymerisable gelling agents (G1 and G2) whereof the gel-sol phase transition point is not less than 37° C., G1 being a gelling agent selected among gelatines and carrageenans and G2 being selected among carrageenans with properties different from the carrageenans selected for G1, and celluloses, which lipisomes have a diameter ranging between 20 nm and 1 mm, preferably ranging between 50 nm and 500 nm and having the form of particulate units with an average particle diameter between 10 mm and 1000 mm, formed by one or several of said liposomes, enclosed in a sheath selected in the group consisting of a dehydrated thermoreversible aqueous gel identical to said internal nucleus aqueous gel, dextrins or a mixture thereof, such that they contain, on an average, $10^{16}$ to $10^{18}$ liposomes per gram of powder.

15 Claims, 8 Drawing Sheets

FOREIGN PATENT DOCUMENTS

| | | |
|---|---|---|
| 0162724 * | 11/1985 | (EP). |
| 0 461 559 A | 12/1991 | (EP). |
| WO 87 01587 A | 3/1987 | (WO). |
| 95/23592 * | 9/1995 | (WO). |
| WO 95 27477 A | 10/1995 | (WO). |

* cited by examiner

POWDER COMPOSITIONS OF UNILAMELLAR LIPOSOMES

This application is a 371 of PCT/FR98/01203 filed Jun. 11, 1998.

The present invention relates to pulverulent compositions of stabilized unilamellar liposomes, which comprise at least one external lipid phase and an internal aqueous polar nucleus which is gelatinized at ambient temperature, to the process for preparing them and to their applications as nutritional supplements and in pharmaceutical compositions (action on lipaemia).

Liposomes having an internal gelatinized nucleus, which are in suspension in aqueous medium and which contain low concentrations of gelatinizing substances have been described by J. C. Hauton, who has termed them lipogelosomes®. He has, in particular, developed a process for manufacturing such liposomes or lipogelosomes® (European Patent 0 393 049), which differ from conventional liposomes in that the encapsulated aqueous phase is present in semi-solid gel form and not in liquid form, and this prevents the liposomes from fusing when collisions occur. These lipogelosomes® are produced entirely from natural substances, thereby minimizing the risk of intolerance. In particular, in the abovementioned European Patent 0 393 049, these lipogelosomes® consist of one bilayer interfacial phase, in the case of the unilamellar lipogelosomes®, or of a multiplicity of bilayer interfacial phases, which are superimposed concentrically, in the case of the multilamellar lipogelosomes®, and of a gelatinized encapsulated internal aqueous polar phase in which the gelatinized substance, which may or may not be polymerizable, is selected from polysaccharides, polypeptides or polyacrylamides; for example, the non-polymerizable gelatinizable substance is selected from gelatin, agarose or carrageenans, and the polymerizable gelatinizable substance is selected from polyacrylamide gels. These lipogelosomes® possess a stability which is significantly increased as compared with the liposomes of the prior art, particularly because of the absence of interparticulate fusion during collisions.

However, they suffer from the disadvantage of being present in a liquid form which is not suitable for preparing solid formulations which are easy to store and administer.

The Applicant has now found, in particular, that, by selecting the lipids of the external lipid phase on the one hand, and the gelatinizing agents, on the other hand, it is possible to prepare stabilized pulverulent lipogelosomes® which exhibit particularly favourable properties, as a nutritional supplement and as a medicament which is intended to be administered by the oral route, in the prevention of hyperlipaemias (hypercholesterolaemias or hypertriglyceridaemias); this is because these stabilized pulverulent lipogelosomes® can either by administered directly by the oral route or be easily dissolved in an aqueous phase at the time of their use.

Cardiovascular diseases are the prime cause of mortality and morbidity in France, as in all the industrialized countries, and represent a real financial burden (30 thousand million francs in 1992). The figures are alarming: 36.4% of all deaths are due to cardiovascular diseases, including 20% due to heart disease and 12% due to strokes. By way of comparison, the next in line are deaths due to the various cancers and violent deaths (accidental or voluntary), in the respective proportions of 24.2% and 9.4%. Such a high incidence of cerebrovascular and cardiac illnesses in western civilisations makes atherosclerosis the prime socioeconomic scourge in the sphere of health.

A long-term prophylaxis is therefore required. It is possible to decrease cholesterolaemia by means of a hypolipidic regime which may or may not be combined with pharmacological products. A method which is widely used in subjects at risk (persons having a cholesterolaemia which is too high) is to sequester the bile salts in the intestine using cholestyramine, and studies have shown that chronic treatment with this synthetic resin decreases the frequency of cardiac illnesses (B M Rifkind, *Atherosclerosis reviews,* 1987, 18, 59–70). However, it appears to be difficult to envisage using such a product for a systematic long-term prophylaxis because it is not easy to handle and exhibits side-effects which are poorly accepted by patients.

While a strict hypolipidic regime appears to be the most efficient means for treating a constituted atherosclerosis, experience shows that this is more often than not impossible because sacrificing gastronomic pleasure is an attack on the quality of life and is, furthermore, difficult to apply in the context of the daily activities of modern societies of developed countries.

Use is made of other lipid-lowering agents which act on the internal environment, such as inhibitors of HMG CoA reductase, which decrease the synthesis of endogenous cholesterol and increase the hepatic receptors for atherogenic lipoproteins, thereby reducing their concentration in the plasma (MS Brown et al., *Atherosclerosis reviews,* 1987, 18, 85–93).

However, applying medicinal preventive measures in apparently healthy subjects having a blood lipoproteinogram which is within so-called "normal" limits is questionable because of the side-effects.

A long-term prophylaxis of atherosclerosis which can be applied at population level involves the necessity of having available products which are effective over the long term, which are easy to handle and which exhibit a minimum of unwanted side-effects.

Sensible dietetic measures should therefore be supplemented with actions at intestinal level whose purpose is to decrease the lipolysis of triglycerides into free fatty acids and monoglycerides and to reduce the production of the micellar phase, from which they and cholesterol are absorbed.

The alimentary triglycerides, whose hydrolysis begins in the stomach (sublingual and gastric lipases) and continues in the duodenum (pancreatic lipase) are organized in the proximal intestinal medium in the form of an emulsion whose monolayer interfacial phase, which is in the main formed by the alimentary and biliary phospholipids (G Nalbone et al., *Lipids,* 1974, 9, 765–770), incorporates the products of lipolysis (monoglycerides and free fatty acids) as well as a fraction of the bile salts. The intestinal interfacial phase is unable to dissociate into micelles until the concentration of detergent molecules (bile salts, ionized fatty acids and lysophospholipids) reaches a certain threshold (critical micellar concentration).

In order strongly to inhibit the intestinal lipolysis of triglycerides and to reduce or even suppress the formation of the micellar phase from which the lipolysis products are absorbed, J. C. Hauton has found (Cah. Nutr. Diet., 1990, 25, 2, 87–91) that it is necessary:

to divert a part of the digestive lipases from the interfacial phase of the particles of the lipid emulsion by combining them on a competing interfacial phase; and to divert a sufficient quantity of bile salts onto the said competing interfacial phase so as to lower their concentration below a given threshold in order to prevent the micellar phase being produced.

The problem to be solved therefore consists in getting an atoxic competing interfacial phase, which exhibits the maximum surface area while having the smallest possible volume, into the proximal intestine during the digestive phase. The present structure which is most suitable is that of small unilamellar liposomes.

From an industrial perspective, and for reasons of handling and storage, such liposomes should be stable. The pulverulent stabilized liposome compositions according to the invention provide an effective solution to this problem, on the one hand because of the presence of the gelatinized internal aqueous nucleus and, on the other hand, due to the fact that they are present in the form of a powder which can either be administered directly by the oral route or easily be dissolved in an aqueous phase at the time of its use.

Consequently, the Applicant has set itself the objective of providing a stable, pulverulent, liposome-based composition which more satisfactorily meets the requirements of practice than do the compositions of the prior art in that, in addition to having a significantly improved stability, it is effective both in preventing and in treating hyperlipaemias.

The present invention relates to a pulverulent composition which is intended for oral administration and which is characterized:

in that it essentially consists of unilamellar liposomes which comprise an external lipid phase which essentially consists of class 4 lipids (phospholipids), to the exclusion of class 3 substances (cholesterol, non-ionized long-chain fatty acids) and class 5 substances (bile salts, derivatives of fusidic acid) and an internal aqueous nucleus forming a temperature-reversible aqueous gel which radiates out up to the external lipid phase, which internal aqueous nucleus essentially consists of a mixture M of at least two different non-polymerizable gelatinizing agents G1 and G2 whose gel-sol phase transition point is higher than or equal to 37° C., with G1 being a gelatinizing agent which is selected from gelatins and carrageenans, such as kappa-carrageenans, and G2 being selected from carrageenans whose properties are different from the carrageenans selected for G1, such as iota-carrageenans, and celluloses, such as hydroxypropylcellulose, which liposomes have a diameter of between 20 nm and 1 mm, preferably of between 50 nm and 500 nm; and in that it is present in the form of particulate units which have a mean diameter of between 10 mm and 1000 mm and which are formed from one or more of the said liposomes which is/are surrounded by a matrix which is selected from the group consisting of a dehydrated temperature-reversible aqueous gel which is identical to the aqueous gel of the said internal nucleus, dextrins or a mixture thereof, such that it comprises, on average, from $10^{16}$ to $10^{18}$ liposomes/g of powder.

The use of such pulverulent liposome compositions in the prevention and therapy of atherosclerosis and obesity can prove to be very useful in rendering less severe, and therefore more acceptable, the hypolipidic regimes which are prescribed for patients who are being treated for these disorders.

Surprisingly, these pulverulent compositions retain all the integrity of the lipogelosomes® which they contain and which remain stable over time, both in pulverulent form and when they are placed in suspension, as a result of the preservation of the integrity of the component lipids (no degradation product) and the preservation of the integrity of the characteristics of the gelatinizing agents, in particular of the G1 and G2 mixture (viscosity, gel strength and breaking force, molecular masses). They thus contain stabilized pulverulent lipogelosomes®.

The gelatinizing agents G1 and G2 differ, in particular, with regard to viscosity, molecular mass and gel-sol transition point (that is melting point). In the case of the G1 gelatinizing agents, this temperature is lower than or equal to 45° C., whereas it is higher than or equal to 45° C. in the case of the G2 gelatinizing agents.

The mixture M of at least two gelatinizing agents G1 and G2, as defined above, exhibits texturometric characteristics (gel strength and breaking force) which are particularly favourable from the point of view of the stability of the liposomes which are obtained. Thus, at 5° C., the mixture M of at least two gelatinizing agents G1 and G2 preferably exhibits relaxation characteristics of between 70 and 100%, preferably 81–89%, and a breaking force of between 1000 and 1600 g, preferably 1109–1503 g.

According to one advantageous embodiment of the said composition, the said internal aqueous nucleus of the liposomes additionally comprises at least one stabilizing agent of glycosidic nature and/or at least one agent for regulating the osmolarity of the medium and/or at least one surfactant.

Advantageously, the said pulverulent composition comprises, in % (m/m): from 25 to 75% of class 4 lipids, from 5 to 45% of gelatinizing agents, from 0 to 70% of stabilizing agent of glycosidic nature, from 0 to 15% of agent for regulating the osmolarity of the medium, from 0 to 20% of surfactants and from 0 to 15% of dextrin (mainly maltodextrin or cyclodextrin), preferably from 8 to 12%.

In accordance with the invention, one gelatinizing agent fraction is included in the internal aqueous phase of the said lipogelosomes® while another gelatinizing agent fraction forms a matrix around the external lipid layer of the said lipogelosomes®.

According to another advantageous embodiment of the said pulverulent composition, it comprises from 70 to 95% of gelatinizing agent G1 and from 5 to 30% of gelatinizing agent G2.

According to another advantageous embodiment of the said pulverulent composition according to the invention, the stabilizing agent of glycosidic nature is sucrose, trehalose or any other protective agent.

According to another advantageous embodiment of the said pulverulent composition according to the invention, the lipids which constitute the external lipid phase of the said liposomes preferably comprise from 20 to 25% of phosphatidylcholine, from 10 to 18% of phosphatidylethanolamine and from 9 to 15% of phosphatidylinositol.

The said phospholipids are in the main obtained from soybean lecithins having a high content of phospholipids.

As an alternative, the phospholipids consist of purified phospholipids, either on their own or in a mixture, preferably in the same proportions as those defined above.

The present invention also relates to a process for preparing a pulverulent composition according to the invention in which the external matrix of the particulate units comprises a temperature-reversible aqueous gel fraction, characterized in that it comprises the following steps:

(1) preparing a dispersion of liposomes having a gelatinized internal nucleus (lipogelosomes®) in aqueous phase by (a) preparing a solution of at least one suitable gelatinizing agent, in particular a mixture M of gelatinizing agents G1 and G2, by dissolving the said gelatinizing agents, while stirring slowly, at a temperature which is higher than the gel-sol phase transition temperature of the said gelatinizing agents, in an aqueous solution, (b) incorporating lipids into the solution obtained in (a), while slowly stirring the mixture, over a period of less than 5 hours, preferably in vacuo and forming an emulsion, and (c) obtaining the dispersion of liposomes having a gelatinized internal nucleus (lipogelosomes®) in an aqueous phase containing the said gelatinizing agents by rapidly stirring the emulsion obtained in (b), preferably in vacuo, and (2) obtaining the pulverulent product by suitable direct drying of the resulting dispersion.

According to one advantageous embodiment of the said process, the drying is carried out by atomization, coacervation, thin film or granulation.

The present invention also relates to a process for preparing a pulverulent composition according to the invention, in which the external matrix of the particulate units comprises a temperature-reversible aqueous gel fraction and/or a dextrin, characterized in that it comprises the following steps:

(1) preparing a dispersion of liposomes having a gelatinized internal nucleus (lipogelosomes®) in aqueous phase by (a) preparing a solution of at least one suitable gelatinizing agent, in particular a mixture M of gelatinizing agents G1 and G2, by dissolving the said gelatinizing agents, while stirring slowly, at a temperature which is higher than the gel-sol phase transition temperature of the said gelatinizing agents, in an aqueous solution, (b) incorporating lipids into the solution obtained in (a), while slowly stirring the mixture, over a period of less than 5 hours, preferably in vacuo and forming an emulsion, and (c) obtaining the said dispersion of liposomes having a gelatinized internal nucleus (lipogelosomes®) in an aqueous liquid phase containing the said gelatinizing agents, by rapidly stirring the emulsion obtained in (b), preferably in vacuo, (2) at least partially removing the aqueous liquid phase which contains the said gelatinizing agents and in which the said liposomes are dispersed, (3) adding at least one suitable dextrin, and (4) obtaining the pulverulent product by drying by atomization the product obtained in (3).

According to an advantageous embodiment of this process, the step (2) of at least partially removing the aqueous liquid phase containing the said gelatinizing agents is carried out by dilution and/or by filtration.

In conformity with the preparation processes according to the invention, the aqueous solution in step (a) additionally comprises an agent for regulating the osmolarity of the medium (for example 0.9% NaCl) and/or a stabilizing agent of glycosidic nature and/or a surfactant.

Surprisingly, these processes make it possible to obtain a pulverulent composition of stable liposomes having a gelatinized internal phase (lipogelosomes®) during the course of a single step consisting of a phase of maturation (in the sense of ripening) of the constituents in aqueous phase, at a slow rate, and then a phase of dispersion (formation of the lipogelosomes®) at a rapid rate, and comprise a step during which a stable dispersion of lipoogelosomes®is obtained in liquid phase, which dispersion has a homogeneous morphology and is suitable for being subjected to the drying step; more specifically, the said dispersion of liposomes having a gelatinized internal nucleus exhibits the following morphology:

vesicular structure having a diameter of between 20 nm and 1 mm, preferably between 70 and 200 nm, negative staining microscopic observations, cryofracture, cryotransmission and atomic force microscopy: vesicles or assemblies of vesicles having the characteristic appearance of phospholipid bilayers; the negative staining makes it possible to observe the more or less pronounced presence of the mixture M of gelatinizing agents enveloping the external phospholipid layer, and a polydispersity of the liposomes having a gelatinized internal nucleus of between 10 and 55%, preferably of between 30 and 50%.

A process of this nature has the advantage of being reproducible and completely adaptable to industrial scale.

It furthermore enjoys the advantage of being less cumbersome to implement than are the processes of the Prior art, in which a step of sonication, of extrusion or of removal of detergents is required, as described in European Patent 0 393 049.

According to another advantageous embodiment of the said processes, step (b) is preferably carried out at a shearing speed of less than 200 $s^{-1}$; as a general rule, the shearing speed is given by the following ratio: speed of the stirring unit/distance between the internal wall of the reactor and the distal end of the stirring blade (also termed "air gap").

The present invention also relates to a nutritional supplement which is suitable for regulating cholesterolaemia and triglyceridaemia, characterized in that it comprises a pulverulent composition as defined above, which may or may not be combined with an appropriate excipient.

The present invention also relates to pharmaceutical compositions which are intended to be administered orally and which comprise a pulverulent composition according to the invention and at least one appropriate vehicle; these compositions are particularly suitable for regulating cholesterolaemia and triglyceridaemia or for being used as an adjuvant in treatments which employ one or more active principles which bring about an increase in transaminases or any other toxic marker; this is because the pulverulent compositions of stabilized liposomes according to the invention have a significant effect in resisting an increase in liver GOT and GPT levels.

Both the nutritional supplement and the pharmaceutical compositions can be present either in a solid form (capsule, tablet or powder to be dissolved in water) or in a liquid form (pulverulent composition according to the invention which is redissolved in an aqueous solution). These forms are suitable for being administered orally.

Advantageously, both the nutritional supplement and the pharmaceutical compositions according to the invention are intended to be administered at a unit dose which corresponds to a unit dose of phospholipids constituting the lipogelosomes® according to the invention of between 0.01 and 0.07 g/kg, that is a daily dose of between 0.03 and 0.2 g of phospholipids constituting the lipogelosomes® per kg of body weight, administered in 2 or 3 subdoses.

In addition to the abovementioned provisions, the invention additionally comprises other provisions which will emerge from the description which follows and refers to examples of implementing the process which is the subject-matter of the present invention and to the attached drawings, in which:

FIG. 1 shows the distribution, in per cent, of the radiolabelled lipid classes (FA: fatty acids; MG: monoglycerides; DG: diglycerides; TG: triglycerides) which were present in the stomach contents of rats which were sacrificed after 2 hours of digestion;

FIG. 2 shows the percentages of radiolabelled lipids which were found in the intestinal lumen as compared with the lipid quantity (in dpm) which was emptied from the stomachs of rats which were sacrificed after 2 hours of digestion (int. seg.: intestinal segment);

FIG. 3 shows the distribution, in per cent, of the radio-labelled lipid classes (FA: fatty acids; MG: monoglycerides; DG: diglycerides; TG: triglycerides) which were present in the intestinal lumen of rats which were sacrificed after 2 hours of digestion (int. seg.: intestinal segment);

Figure 1A:
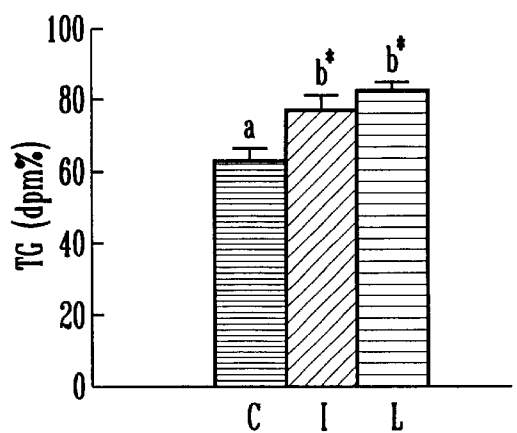
Figure 1B:
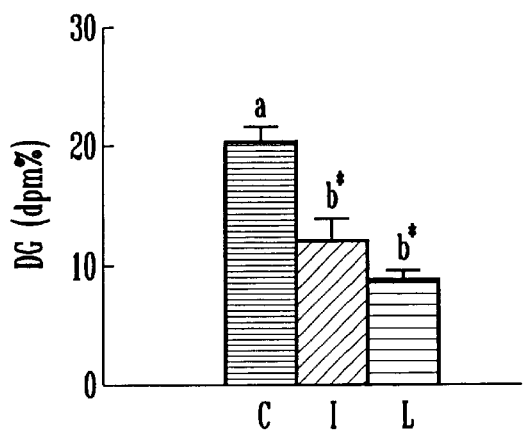
Figure 1C:
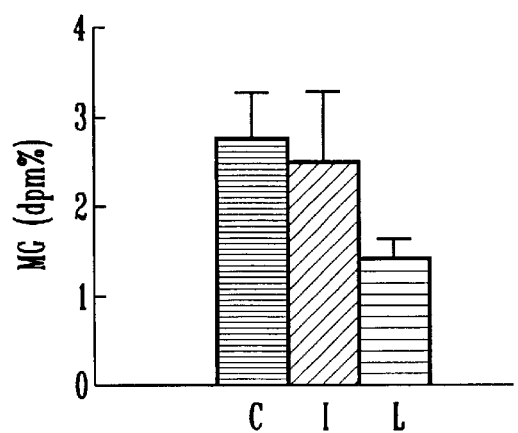
Figure 1D:
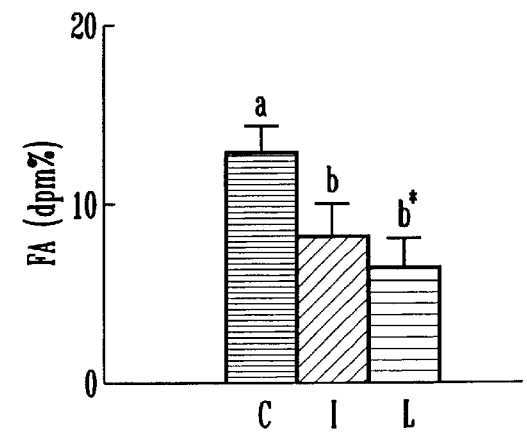

It should, of course, be understood, nevertheless, that these examples are given solely by way of illustrating the subject-matter of the invention, to which they in no way constitute a limitation.

EXAMPLE 1

Texturometry Measurements on the Mixture of the Gelatinizing Agents G1 and G2 a) Materials and Methods

The measurements are carried out on a Rheo TA-XT2i appliance. The study concerns the behaviour of gels which consist of a mixture of gelatin and iota- and kappa-carrageenans during breaking and relaxation tests.

Concentrations of the Samples 7.5% (w/v) mixture of gelatin/iota-/kappa-carrageenans (80/17.5/2.5) in a medium consisting of 5 mM $Na_2HPO_4$ and 0.9 or 2% NaCl.

Preparing a Solution of Gelatinizing Agents

The sodium chloride is dissolved in a mixer which is fitted with a turbine and a planetary member and which contains purified water (15 minutes at 10 revolutions/minute); the temperature in the mixer is raised to 75° C. (stirring at 10 revolutions/minute for 45 minutes); the gelatinizing agents (gelatin, iota-carrageenans and kappa-carrageenans) are added to the mixer at 75° C.; the stirring turbine is set going at 1500 revolutions/minute; the duration of the dissolution step is approximately 30 minutes; the dissolution is complete when the solution is clear and does not contain any particles in suspension.

Preparing the Samples

For the relaxation test, 45 ml of gel are cast in the heated state in a flat-bottomed Petri dish having an external diameter of 92±2 mm. For the breaking test, 30 ml of gel are cast in the heated state in a flat-bottomed crystallizing dish having an external diameter of 50±2 mm. The gel is obtained by cooling down to a temperature which is lower than or equal to 37° C. The maturation time for the gels, which corresponds to maximum hydration of the gels, is 2.5 days at the temperature of the study and at rest.

Operating Conditions

For the relaxation test, a compression force is applied to the gel for a given time. The mobile element employed is a 25 mm diameter aluminium cylinder which has a pre-speed of 1.0 mm/s, a speed of 0.5 mm/s and a post-speed of 10.0 mm/s. The displacement of the mobile element is 1.0 mm over 30 seconds.

For the breaking test, the mobile element employed is a 10 mm diameter ebonite cylinder having a pre-speed, a speed and a post-speed of 1.0 mm/s. The displacement of the mobile element is 12 mm.

b) Results of a Study Carried Out at 5° C. Using an NaCl Level of 0.9%

Relaxation (%)

minimum value: 81±2.2 maximum value: 89±0.8

Breaking force (g)

minimum value: 1109±25 maximum value: 1503±35 c) Results as a Function of the Temperature and of Different Levels of NaCl

The operating conditions are identical to those described in a) except as regards the displacement of the mobile element which is employed in the relaxation test (displacement equal to 20% of the total thickness of the gel).

Relaxation (%)

at 5° C.

0.9% NaCl: 89±0.8

2% NaCl: 90±0.2 at 25° C.

0.9% NaCl: 32±3.9

2% NaCl: 38±4.4 at 37° C.

0.9% NaCl: 36±3.7

2% NaCl: 40±4.9

Breaking force (g)

at 5° C.

0.9% NaCl: 1413±66

2% NaCl: 1114±143 at 25° C.

0.9% NaCl: 211±2.7

2% NaCl: 173±1.5 at 37° C.

0.9% NaCl: 25.7±2.4

2% NaCl: 45.7±3.9

EXAMPLE 2

Process for Preparing a Pulverulent Composition According to the Invention (LGS) (Having an External Matrix Which Consists of Dehydrated Gelatinizing Agents)

1) Preparing a Dispersion of Liposomes Having a Gelatinized Internal Phase (Lipogelosomes®)

Constituents:

| | |
|---|---|
| Soybean lecithins | 11.915 kg (7.943%) |
| Gelatin B150 | 7.149 kg (4.766%) |
| Iota-carrageenans | 1.565 kg (1.043%) |
| Kappa-carrageenans | 0.222 kg (0.148%) |
| Sucrose | 8.936 kg (5.957%) |
| Sodium chloride | 1.073 kg (0.715%) |
| Purified water | 119.15 kg (79.43%) |
| TOTAL CONTENTS | 150.01 kg (100%). | a) Preparing a Solution of Gelatinizing Agents

The procedure is the same as Example 1. The characteristics of the solution are verified by sampling and the glycosidic stabilizing agent (sucrose) is then added.

b) Incorporating the Phospholipids Into the Solution Obtained in a)

The soybean lecithins are added to the mixer, in which the planetary member is rotating at a speed of 10 revolutions/ minute and the turbine at a speed of 1500 revolutions/ minute, for a period of 5 hours and in vacuo (→emulsion formation)

final dispersion by increasing the stirring speeds of the planetary member (25 revolutions/minute) and of the turbine (2500 revolutions/minute) for a time which is sufficient for obtaining a polydispersity of less than 40%.

This results in a dispersion of lipogelosomes® in aqueous phase.

Studying the samples removed at the end of the dispersion shows vesicular structures having a diameter of 120±30 nm.

Negative staining microscopic observations, cryofracture, cryotransmission and atomic force microscopy: vesicles or assemblies of vesicles having the characteristic appearance of phospholipid bilayers; the negative staining makes it possible to observe the presence of external gelatinizing agent, which is more or less pronounced depending on the method of preparation and/or separation which is selected.

2) Drying the Resulting Dispersion

The resulting dispersion of the lipogelosomes® in aqueous phase is transferred into a drier under vacuum (50–100 mbars) for a period of approximately 4 hours. This results in a relatively homogeneous powder which has a very pale straw-yellow colour and contains grains having a diameter of between 0.1 mm and 1 mm. It is also possible to use other drying methods.

Under the electron microscope, the lipid vesicles are seen to be retracted on themselves as a result of the dehydration. In addition, it can be seen that, whereas, in the liquid state, the LGSs are often aggregated inside a homogeneous gelatinized matrix, in an environment of numerous isolated vesicular structures, the drying step transforms this gelatinous matrix into dry filaments of gelatinizing agent both on the surface of the aggregates and on the surface of the isolated vesicular structures: the Applicant is of the view that this difference in morphology is probably at the origin of the differences in behaviour of the dry structures, as compared with the moist LGS form, with regard to the metabolism of the lipids.

As an alternative, the drying is carried out as follows: the dispersion of lipogelosomes® in aqueous phase is distributed directly onto a rotating drum drier (temperature of the drums: 120–150° C., speed of rotation, 3–6 revolutions/ min). The resulting "shavings" are then ground and calibrated on a suitable grid. This then results in a lipogelosome® powder (also termed LGS below) which possesses the above-defined characteristics.

EXAMPLE 3

Process for Preparing a Pulverulent Composition According to the Invention (LGS) (Having an External Matrix Comprising Maltodextrins)

1) Preparing a Dispersion of Liposomes Having a Gelatinized Internal Phase (Lipogelosomes®)

Constituents:

| Soybean lecithins | 11.915 kg (7.943%) |
|---|---|
| Gelatin B150 | 7.149 kg (4.766%) |
| Iota-carrageenans | 1.565 kg (1.043%) |
| Kappa-carrageenans | 0.222 kg (0.148%) |
| Sucrose | 8.936 kg (5.957%) |
| Sodium chloride | 1.073 kg (0.715%) |
| Purified water | 119.15 kg (79.43%) |
| TOTAL CONTENTS | 150.01 kg (100%). | a) Preparing a Solution of Gelatinizing Agents

The procedure is the same as in Example 2.

b) Incorporating the Phospholipids Into the Solution Obtained in a)

The soybean lecithins are added to the mixer, in which the planetary member is rotating at a speed of 10 revolutions/ minute and the turbine at a speed of 1500 revolutions/ minute, for a period of 5 hours and in vacuo (→emulsion formation).

final dispersion by increasing the stirring speeds of the planetary member (25 revolutions/minute) and of the turbine (2500 revolutions/minute) for a time which is sufficient for obtaining a polydispersity of less than 40%.

This results in a dispersion of lipogelosomes® in aqueous phase.

Studying the samples removed at the end of the dispersion shows vesicular structures having a diameter of 120±30 nm.

Negative staining microscopic observations, cryofracture, cryotransmission and atomic force microscopy: vesicles or assemblies of vesicles having the characteristic appearance of phospholipid bilayers; the negative staining makes it possible to observe the presence of external gelatinizing agent, which is more or less pronounced depending on the method of preparation and/or separation which is selected.

2)

The dispersion of LGS in external gelatinizing medium is diluted 1/10 with a 0.9% solution of NaCl and then filtered through a 300 kDa or 500 kDa filter ("Open Channel" tangential filtration system from PAL FILTRON) at 37° C. After concentrating the LGS, a dispersion is obtained whose content of dry matter varies between 37 and 50% (m/v). A quantity of maltodextrin equivalent to 4–6% (m/m) is added. An atomization (for example using an NIRO pilot atomizer) is carried out after dissolving the maltodextrin and homogenizing the mixture. This then results in particulate units in which the external matrix includes maltodextrins and whose composition is approximately as follows:

LGS concentrated to 44.6% dry matter 1500 g

Maltodextrin 80 g

Total theoretical LGS atomizate 830 g

Quantity obtained 760 g (yield 84%).

The atomization is carried out under the following conditions:

air inflow temperature: between 180° C. and 200° C.

air outflow temperature: between 80° C. and 95° C.

pressure at the top of the turbine: approximately 4 bars outflow temperature of the solution to be atomized: between 20° C. and 45° C.

EXAMPLE 4

Effects of Ingesting a Pulverulent Composition According to Example 2 on the Intestinal Absorption of Alimentary Lipids in Rats in the Post-prandial Period This study is carried out in normolipidaemic rats in the post-prandial period. The normolipidaemia makes it possible to study the true effects of the lipogelosomes® without any interaction with the metabolic disturbances which are engendered by a pathological state. The post-prandial period enables the mechanisms to be studied, providing a "photograph" of the effects of the lipogelosomes® at a given point of time during digestion.

MATERIALS AND METHODS

Animals and Regimes

Animals

The official French (No. 87-848, dated Oct. 19, 1987) and European (No. 86-609, dated Nov. 24, 1986) regulations for the care and use of laboratory animals were respected.

The animals are male Wistar rats (Iffa-Crédo, l'Arbresle, France) weighing 300 grams. During an adaptation period of 10 days, they were placed in cages in an air-conditioned room (21° C. temperature, 50% humidity) having a light-dark cycle of 12 h–12 h; water and feed were supplied ad libitum. 48 hours before the experiment, the rats were placed in holding cages and were given a dietary regime of 50 g of glucose/l. 24 hours before the experiment, they are placed on a starvation diet, consisting of only water, which was given ad libitum, in order to avoid coprophagia.

In this way, the stomachs of the rats are free of any material prior to the test meals being intubated.

Six groups of rats are made up in a random manner: two control groups (C), two "lipogelosome®" groups (LGS) and two "ingredient" groups (I) which are sacrificed, either 2 hours after digestion or 24 hours after digestion. Because of experimental constraints, the number of rats varies depending on the groups.

Test Meals

Each test meal consists of a lipid emulsion to which lipogelosomes® (LGS group), the ingredients of the lipogelosomes® (I group) or sodium chloride (C group) were added at the time of use.

The Lipid Emulsion 522.5 mg of a mixture containing triolein, cholesterol and soybean lecithins (Table I) were added to an aqueous solution of sodium chloride, sucrose and albumin. The preparation is emulsified by magnetic stirring and sonication. It is renewed each week. The diameters of the particles of this emulsion were checked every day using a granulometer (Capa 700, Horiba, Kyoto, Japan). No difference was observed from one day to the next, with the mean diameter being 2.97 $\mu$m.

The specific radioactivities of the $^{14}$C-triolein and the $^3$H-cholesterol were 68.45 kBq/mmol and 4.27 kBq/mmol, respectively, in each test meal.

The Lipogelosomes®

A pulverulent composition in accordance with Example 2 is dissolved in water in order to obtain a phospholipid concentration of 39.47 mg/ml; the diameters of the suspended lipogelosomes®, which are checked by granulometry and by electron microscopy, are stable and approximately 164.9 nm (mean value).

The Ingredients of the Lipogelosomes®

The starting materials constituting the lipogelosomes®, as specified in Example 2, are used. The phospholipids and the gelatinizing mixture were prepared separately.

Administering the Test Meals

In the case of the LGS and I groups, 2.2 ml of the lipogelosome® preparation or of the ingredients were mixed with 1.5 ml of the lipid emulsion in a syringe at the time of use. In the case of the C groups, an equivalent quantity of sodium chloride was added to the lipid emulsion.

The ratio of alimentary triglycerides/phospholipids in the total quantity ingested is 40 for all the groups and corresponds to the ratio which is observed in human nutrition. However, in order to take account of this value, the test meals for the animals treated with LGS or I contain a reduced alimentary contribution of lipids as a consequence.

The rats were intubated with polyethylene catheters using a stomach probe. Before the emulsion was intubated, two aliquots were removed so as to quantify precisely the radioactivity ingested by the rats.

TABLE I

Compositions of the test meals*

| | |
|---|---|
| Distilled water (mg) | 1500.00 |
| Sodium chloride (mg) | 13.50 |
| Sucrose (mg) | 800.00 |
| Bovine serum albumin (mg) | 200.00 |
| Lecithins of the lipogelosomes ®/ ingredients (+ or −) (mg) | 87.50 |
| Lipid mixture | 522.50 |
| Triolein (mg) | 500.00 |
| $^{14}$C-triolein (kBq) | 37.00 |
| Cholesterol (mg) | 10.00 |
| $^3$H-cholesterol (kBq) | 111.00 |
| Soybean lecithin (mg) | 12.50 |

*Bovine serum albumin (fatty-acid-poor): Calbiochem, San Diego, CA. Triolein (99% pure): Serva, Heidelberg, FRG. $^{14}$C-triolein (98.3% pure), 4.1 Gbq/mmol: NEN Research Products, Dupont de Nemours, Paris, France. Cholesterol (99% pure): Sigma, St Louis, MO. $^3$H-Cholesterol (99% pure), 814 Gbq/mmol: NEN Research Products, Dupont de Nemours. Soybean lecithin (90% pure): Frangis, St-Maur, France.

Samples Taken

Blood

After 2 or 24 hours of digestion, the rats were anaesthetized with a ketamine/xylamine (60 mg/kg/7.5 mg/kg) mixture and then sacrificed by exsanguination. The blood was removed by puncturing the abdominal aorta and approximately 10 ml were collected in tubes which contained EDTA, in order to prevent them coagulating.

Table II below lists the conditions under which the different samplings were effected.

TABLE II

| Digestion time | Samples taken | Treatment of the samples | Counting the radioactivity |
|---|---|---|---|
| 2 hours | Blood | centrifugation in order to separate the plasma | direct |
| | Liver | dissolution | direct |
| | Contents of the stomach | homogenization extraction of the lipids and TLC* | direct in org. medium |
| | Contents of the intestine (in thirds) | homogenization extraction of lipids and TLC* | direct in org. medium** |
| | Intestinal mucosa (in thirds) | scraping and homogenization | direct |
| | Contents of the caecum | homogenization | direct |
| 24 hours | Blood | centrifugation in order to separate the plasma | direct |
| | Liver | dissolution | |
| | Contents of the stomach | homogenization | direct |
| | Contents of the intestine | homogenization | direct |
| | Intestinal mucosa | scraping and homogenization | direct |
| | Contents of the caecum | homogenization | direct |
| | Faeces | lyophilization and extraction of the lipids | direct in org. medium |

*TLC: Thin layer chromatography for separating the different lipid classes
**org.: organic.

In the case of the 2 hour digestion time, the results of the measurements of direct radioactivity were expressed as a percentage of the radioactivity found beyond the pylorus of the stomach in order to reduce the influence of gastric emptying, which is variable within one and the same group.

This was not necessary in the case of the rats which were sacrificed at 24 hours of digestion since emptying is then 99.9% for all the rats. The results are therefore expressed in dpm.

RESULTS

1) Effects of the Lipogelosomes® on Lipolysis of the Lipids in the Stomach

As previously observed in animals and humans, the alimentary lipids are partially hydrolysed in the stomachs of the rats. After two hours of digestion, the stomach contents of the three groups C, I and LGS are not significantly different, although of slightly lower magnitude, as far as the rats of the LGS group are concerned (Table III). These results correspond to levels of gastric emptying which are close to those which have previously been found in rats after the consumption of test meals (Gallaher D. et al., Am. J. Physiol., 1985, 249, 184–191).

TABLE III

Stomach contents and gastric emptyings after 2 hours of digestion*

| Group | Stomach contents (% dpm) | Gastric emptying (% dpm) |
|---|---|---|
| Controls (C) | 50.8 ± 8.3 | 49.1 ± 8.3 |
|  | 50.7 ± 4.8 | 49.3 ± 4.8 |
| Lipogelosomes (LGS) | 43.6 ± 5 | 56.4 ± 5 |
|  | 44.3 ± 4.8 | 55.7 ± 4.8 |
| Ingredients (I) | 52.6 ± 4.1 | 47.4 ± 4.1 |
|  | 51.9 ± 3.5 | 48.1 ± 3.5 |

*The results are expressed as a percentage of the radioactivity (in dpm) intubated. The first line relates to $^{14}$C-lipids while the second line relates to $^{3}$H-cholesterol. No significant difference was observed between the groups using the Fisher test ($p < 0.05$).

No difference was observed as regards the quantities of $^{14}$C-lipids and $^{3}$H-cholesterol which were present in the stomachs of the rats of the three groups after two hours of digestion. On the other hand, the same was not the case as regards the quality of the $^{14}$C-lipids, which were subjected to a hydrolysis whose extent varied in accordance with the groups.

FIG. 1 shows the percentages of triglycerides (TG), diglycerides (DG), monoglycerides (MG) and fatty acids (FA) which were found in the stomach contents two hours after intubation of the test meal containing triglycerides. The proportion of triglycerides remained significantly higher when the ingredients (+21.6% as compared with the C group) and the lipogelosomes® (+31.3%) were present in the test meal, contrary to the proportions of the diglycerides and the fatty acids, which are significantly lower. The proportion of monoglycerides is not significantly different between the three groups; however, it has undergone a marked decrease in the stomach contents of the rats belonging to the LGS group (−48.5% as compared with the C group).

The proportions of the lipid classes in the stomach contents of the rats belonging to the Ingredients group are always intermediate between those of the Control and LGS groups.

The cholesterol remains unchanged and does not undergo any transformation at the level of the stomach.

In FIG. 1, each histogram is the mean±SEM of the individual values for each group (C: Controls; I: Ingredients L: Lipogelosomes®). Different letters indicate significant differences (p<0.05) between the groups, as calculated by the Fisher test. An * symbol indicates a significant difference (p<0.05) as compared with the Control group as found using the Schéffe test.

2) Effects of the Lipogelosomes® in the Intestinal Compartment

Figure 2A:
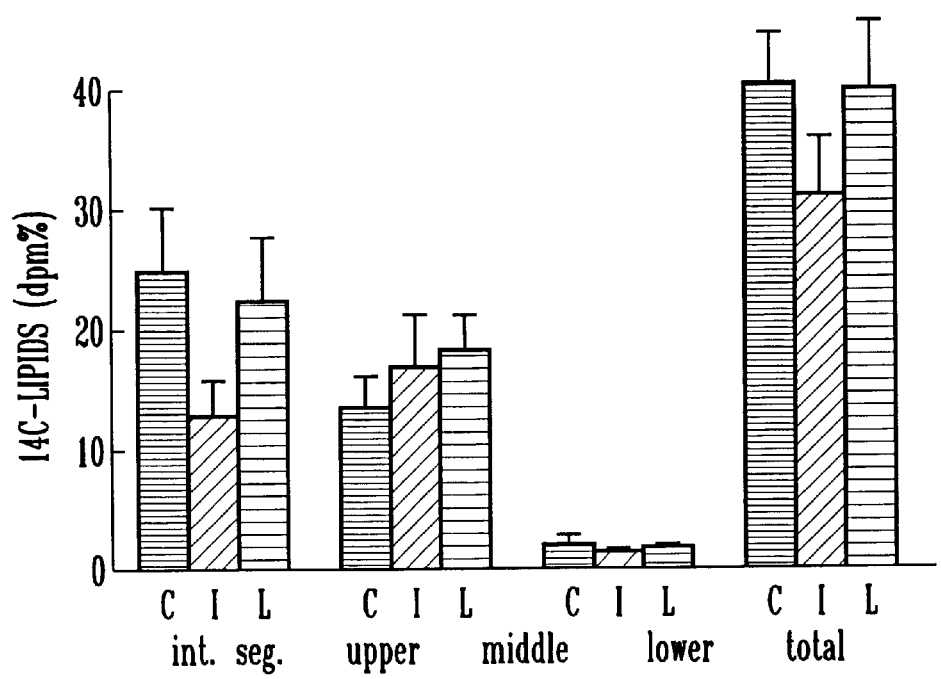
Figure 2B:
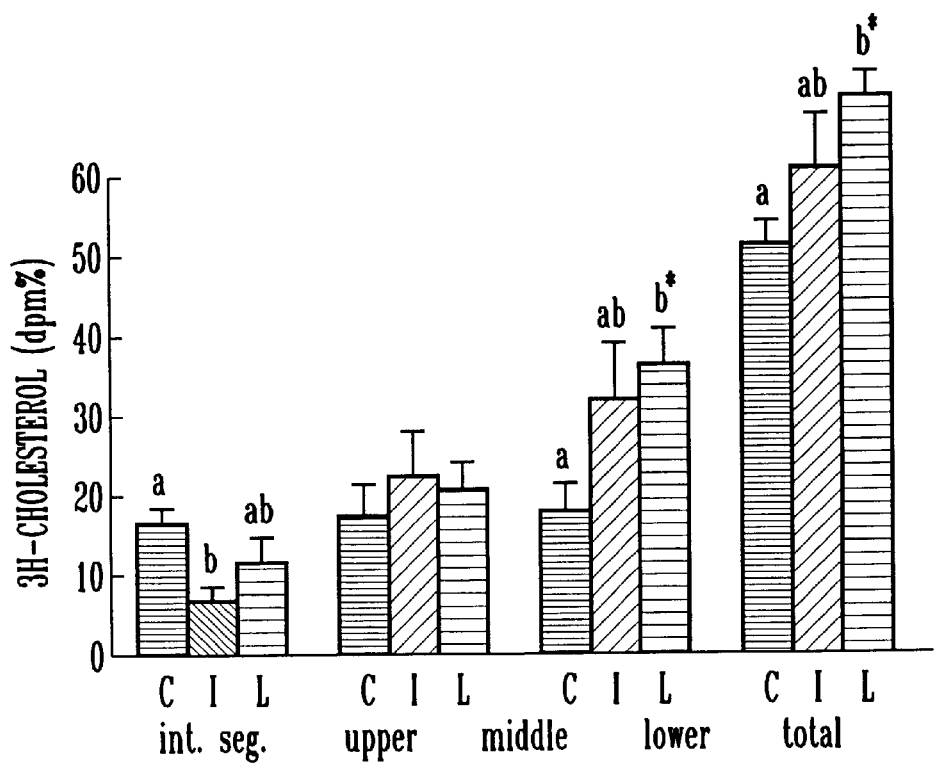
Figure 3A:
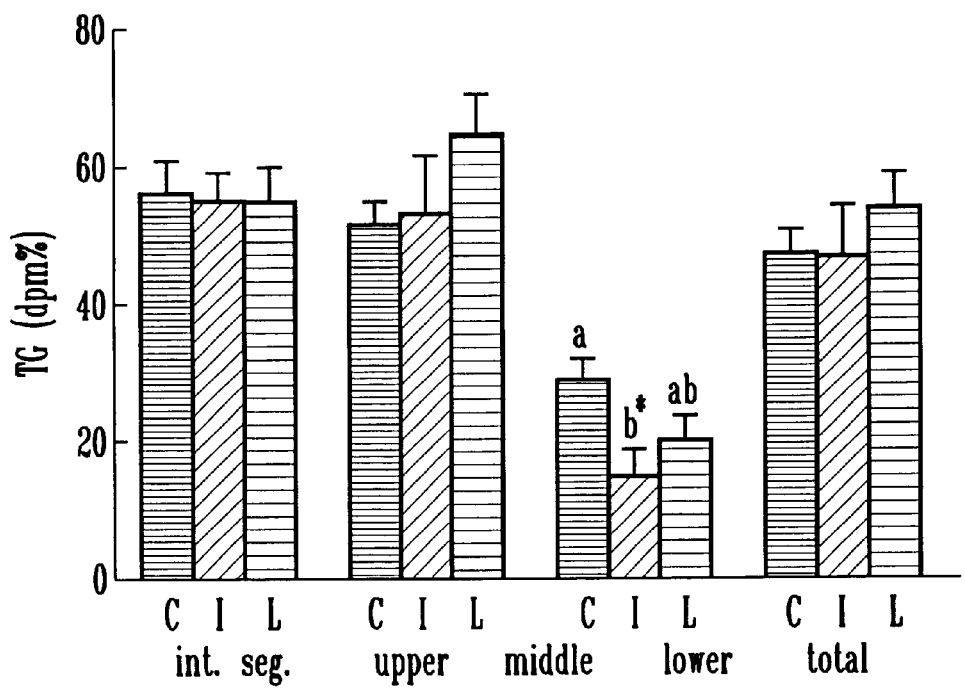
Figure 3B:
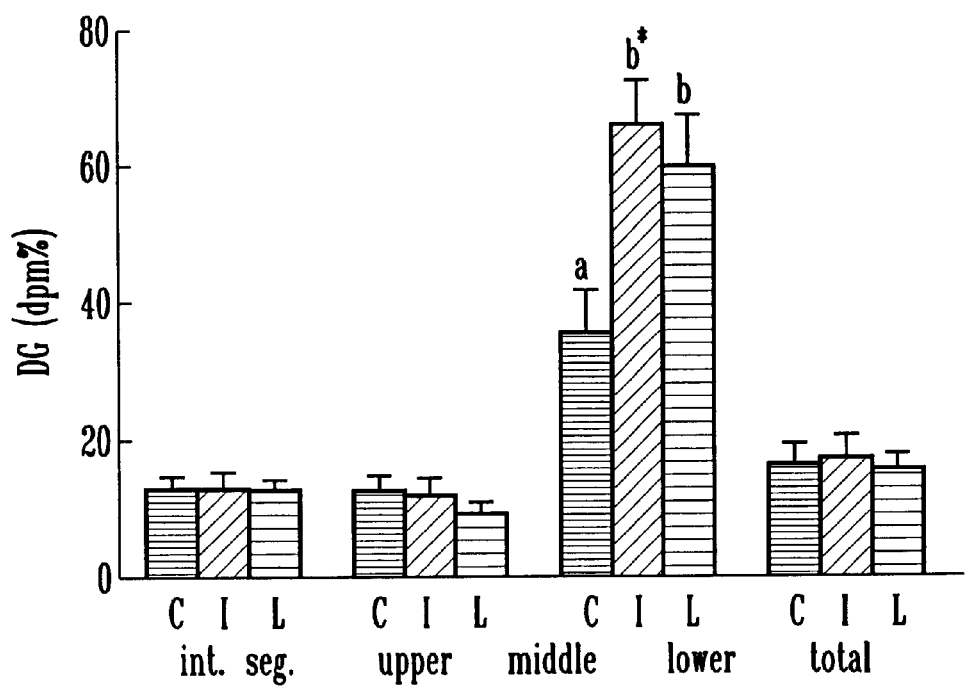
Figure 3C:
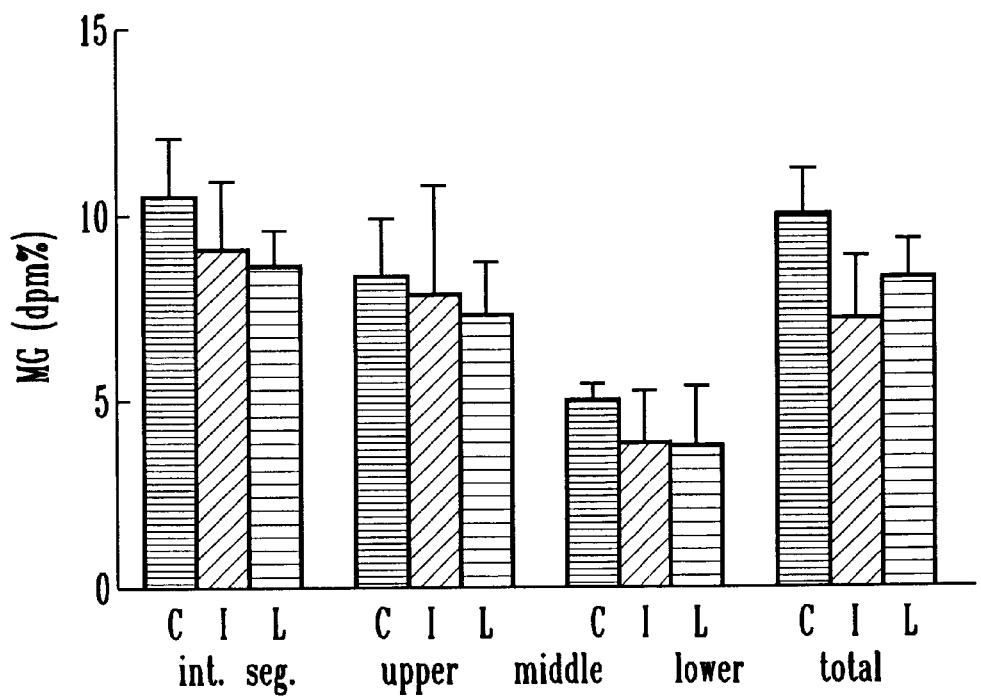
Figure 3D:
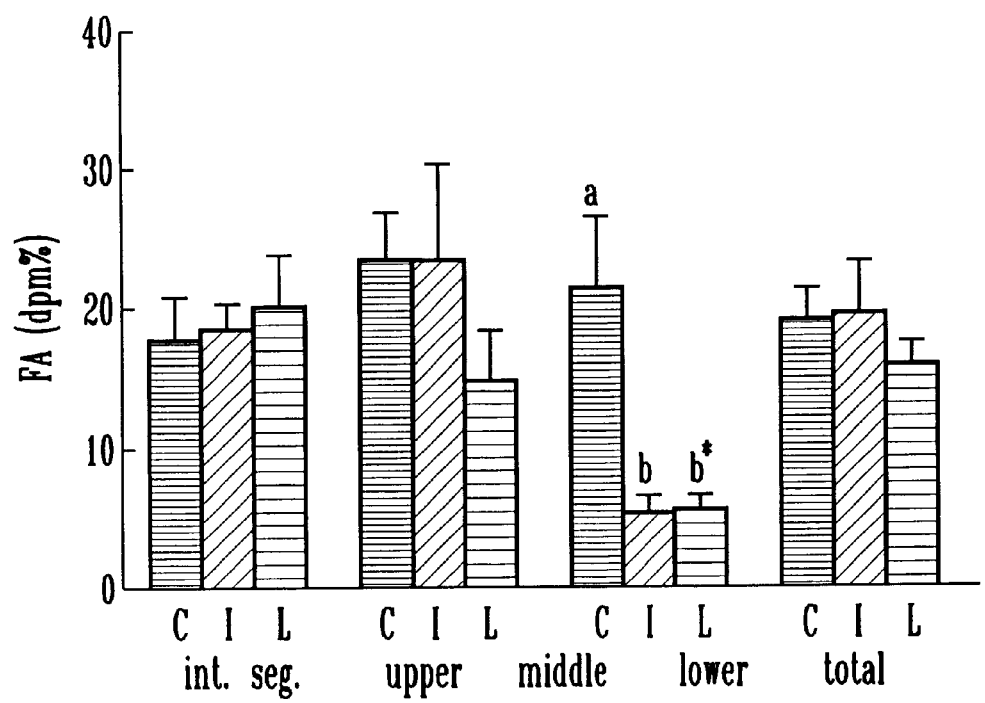

As in the case of the stomach contents, the intestinal contents of the rats which were sacrificed after 2 hours of digestion does not differ significantly between the Control, Ingredients and LGS groups in terms of the quantity of $^{14}$C-lipids. FIG. 2 shows that the distribution of the $^{14}$C-lipids in the three intestinal segments is similar in the case of the Control and LGS groups, with the quantity of $^{14}$C-lipids decreasing from the upper part to the lower part of the intestine. A markedly (but not significantly) lower quantity of $^{14}$C-lipids is found in the intestinal contents of the upper segment and the whole of the intestine of the Ingredients group. In FIG. 2, each histogram is the mean±SEM of the individual values for each group (C: Controls; I: Ingredients; L: Lipogelosomes®). Different letters indicate significant differences (p<0.05) between the groups as calculated by the Fisher test. An * symbol indicates a significant difference (p<0.05) as compared with the Control group as found using the Schéffe test.

The proportions of the different lipid classes which were found in the contents of the intestinal segments were altered in accordance with the test meal which was intubated (FIG. 3). The diglycerides were significantly higher in the lower intestinal segment of the rats belonging to the Ingredients and Lipogelosome® groups. In this same segment, the fatty acids were significantly decreased by the ingredients and the lipogelosomes®. Because of a relatively high degree of intra-group variability, the ingredients and the lipogelosomes® did not give rise to any significant differences with regard to the contents of the upper and middle intestinal segments. In FIG. 3, each histogram is the mean±SEM of the individual values for each group (C: Controls; I: Ingredients; L: Lipogelosomes®). Different letters indicate significant differences (p<0.05) between the groups as calculated by the Fisher test. An * symbol indicates a significant difference (p<0.05) as compared with the Control group as found using the Schéffé test.

As FIG. 2 shows, the distribution of cholesterol along the intestine was altered by the ingredients and the lipogelosomes®. The ingredients significantly decreased the cholesterol present in the intestinal contents of the upper segment (−57.3% as compared with the C group); the lipogelosomes® significantly increased the cholesterol present in the intestinal contents of the lower segment, as well as in the intestinal contents taken overall (+104.5% and +34.4%, respectively, as compared with the C group).

The results for the rats which were sacrificed after 24 hours of digestion do not exhibit any differences between the three groups. The radioactivities which were measured were very low, with the intestine being virtually empty at this time in the digestion.

3) Effects of the Lipogelosomes on the Absorption of the Alimentary Triglycerides and Cholesterol The contents of the intestinal mucosa were sampled and analysed only for the 2 hour digestion time; carrying out this analysis in the case of the 24 hour time would not have been of any relevance since the transit time of the lipids in the enterocytes is short.

Figure 4A:
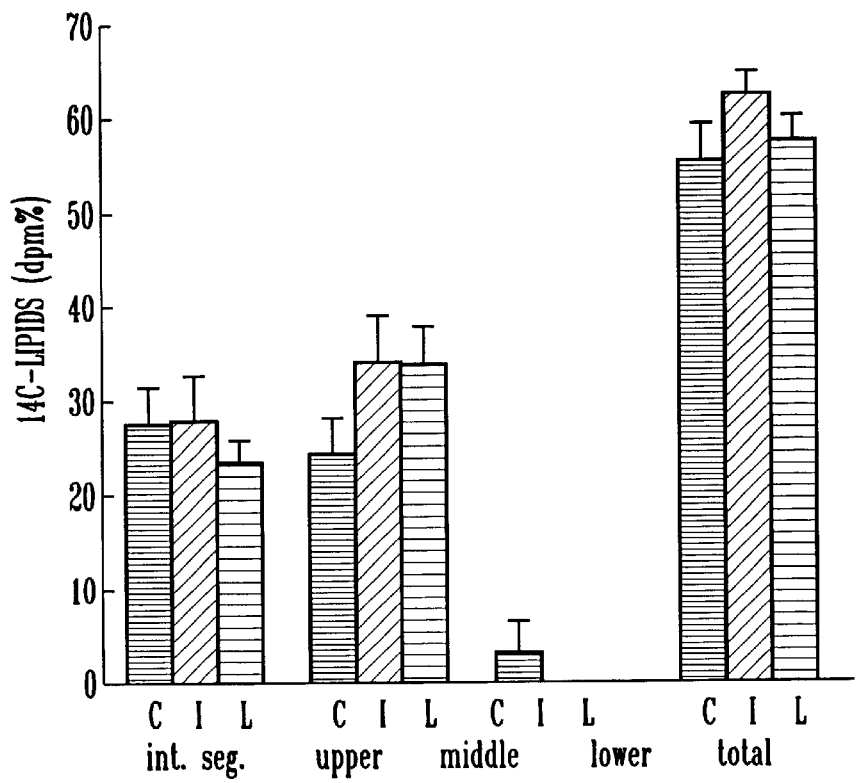
FIG. 4 shows the percentages of radiolabelled lipids which were found in the intestinal mucosa as compared with the lipid quantity (in dpm) which was emptied from the stomachs of rats which were sacrificed after 2 hours of digestion (seg. muc.: segment of the mucosa)
Figure 4B:
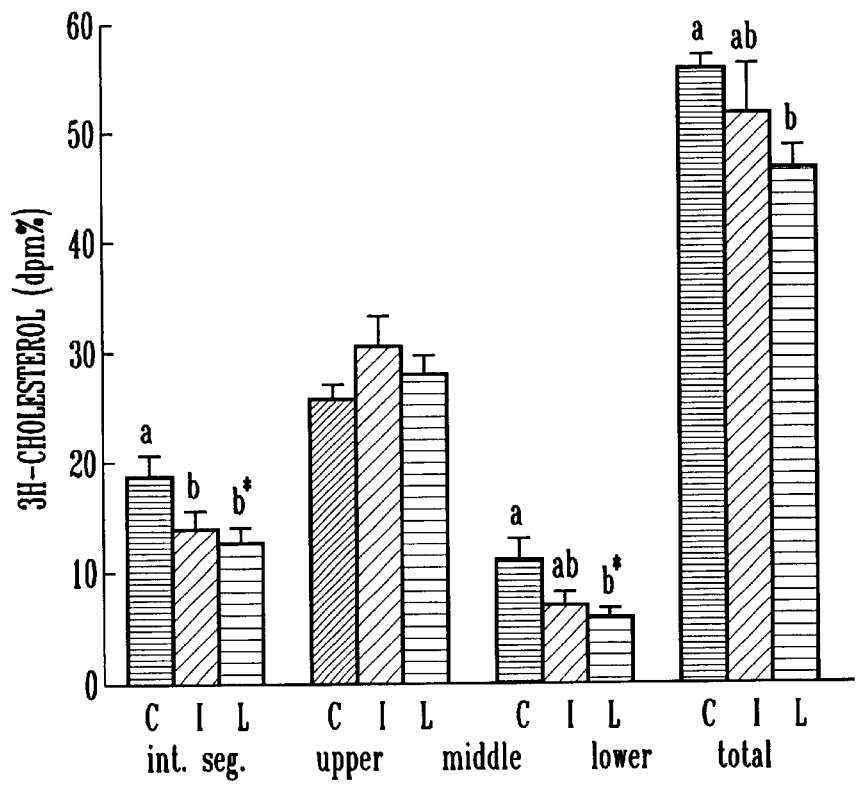

There were no significant differences in the triglyceride content of the cells of the intestinal mucosa between the C, I and LGS groups (FIG. 4).

The absorption of alimentary cholesterol is considerably modified by the presence of the lipogelosomes® in the test meal and, to a lesser degree, by that of their ingredients (FIG. 4). The absorption of cholesterol is significantly decreased by the ingredients within the upper segment of the intestinal mucosa. The lipogelosomes® brought about a significant decrease in the absorption of cholesterol in the upper and lower segments of the mucosa and in the intestinal mucosa taken overall (−32.9%, −47% and −16.8%, respectively, as compared with the C group). In FIG. 4, each histogram is the mean±SEM of the individual values for each group (C: Controls; I: Ingredients; L: Lipogelosomes®). Different letters indicate significant differences (p<0.05) between the groups as calculated by the Fisher test. An * symbol indicates a significant difference (p<0.05) as compared with the Control group when using the Scheffé test.

4) Effects of the Lipogelosomes® on the Plasma Levels of the Lipids

Figure 5A:
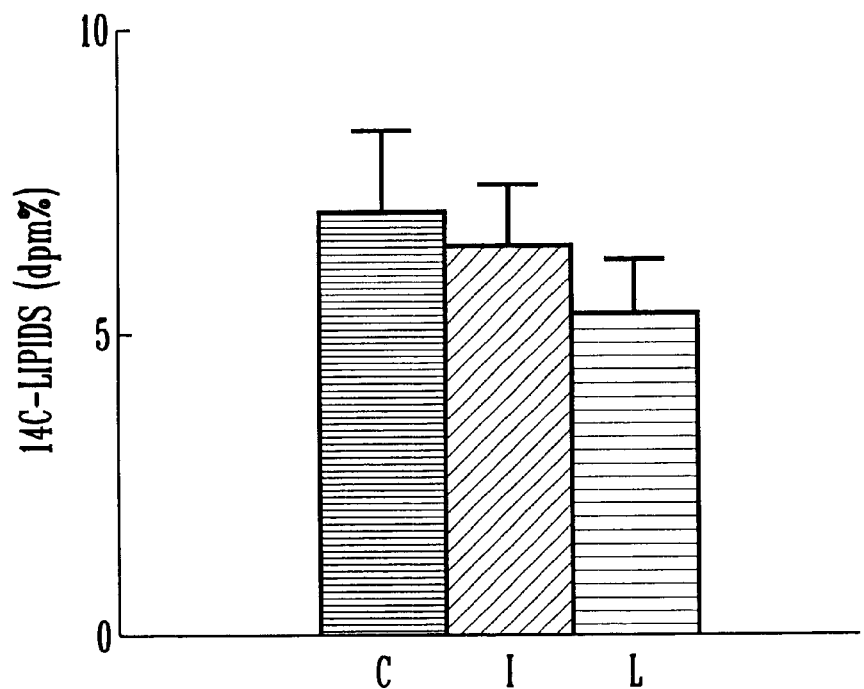
FIG. 5 shows the percentages of radiolabelled lipids which were found in the plasma as compared with the lipid quantity (in dpm) which was emptied from the stomachs of rats which were sacrificed after 2 hours of digestion.
Figure 5B:
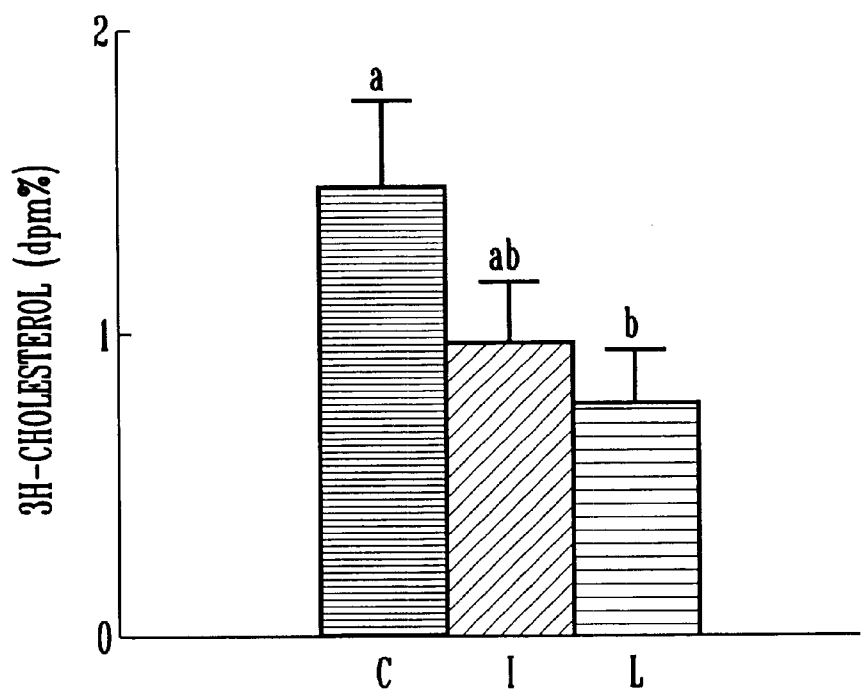

The quantities of $^{14}C$-triglycerides and $^{3}H$-cholesterol in the plasmas of the rats which were sacrificed after 2 hours of digestion are shown in FIG. 5.

While the ingredients and the lipogelosomes® have a tendency to decrease the plasma triglycerides, the differences which are observed are not significant.

The plasma cholesterol is significantly lowered by the lipogelosomes® (−42.6% as compared with the C group). The ingredients have an effect which is similar but not significant as compared with the plasma cholesterol of the rats of the control group.

In FIG. 5, each histogram is the mean±SEM of the individual values for each group (C: Controls; I: Ingredients; L: Lipogelosomes®). Different letters indicate significant differences (P<0.05) between the groups as calculated by the Fisher test. An * indicates a significant difference (p<0.05) as compared with the Control group as found using the Scheffé test.

No difference between the three groups is observed in the case of the 24-hour time.

5) Effects of the Lipogelosomes® on Lipid Metabolism in the Liver

Figure 6A:
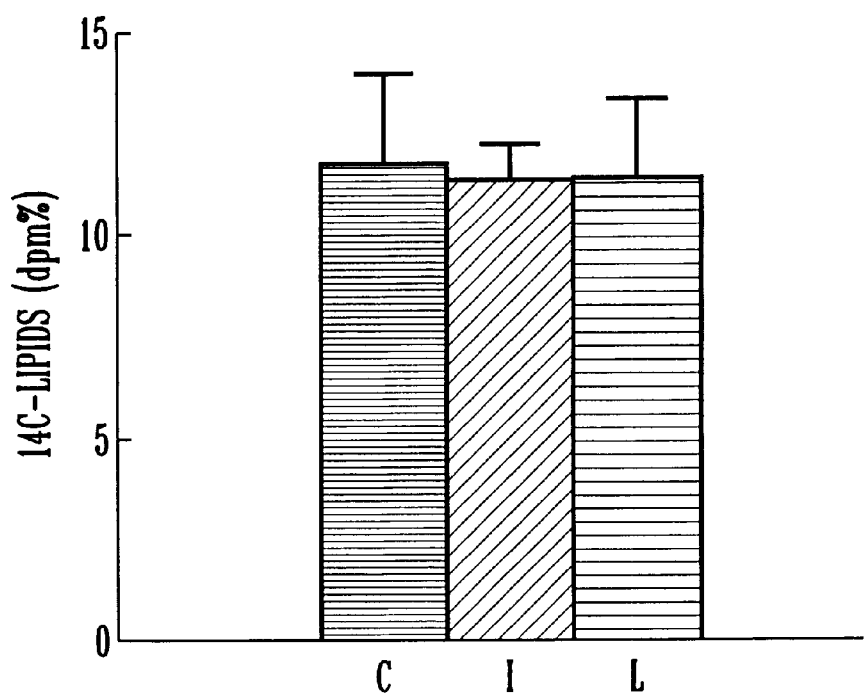
FIG. 6 shows the percentages of radiolabelled lipids which were found in the liver as compared with the lipid quantity (in dpm) which was emptied from the stomachs of rats which were sacrificed after 2 hours of digestion.
Figure 6B:
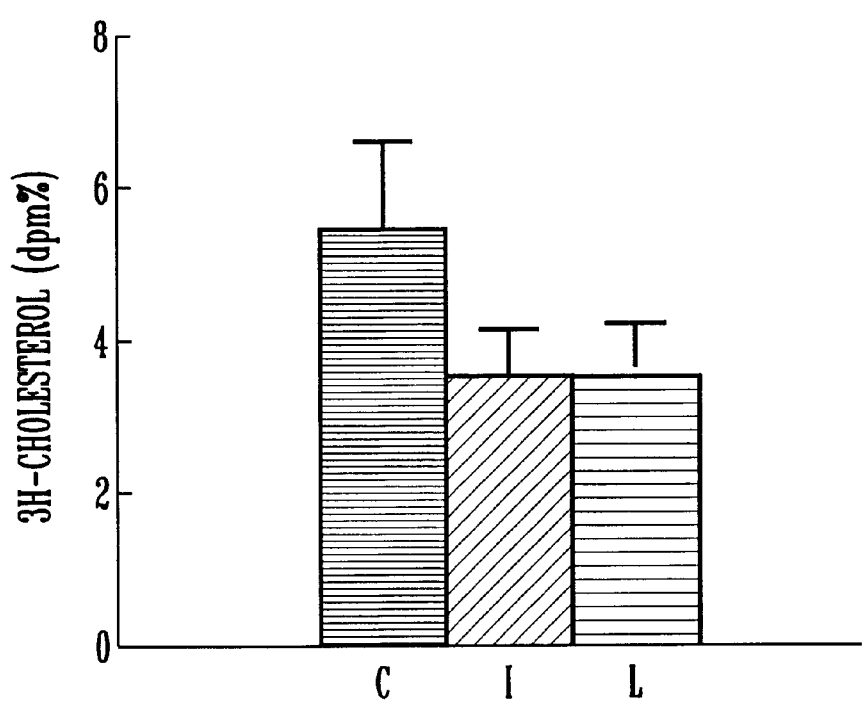

The ingredients and the lipogelosomes® do not have any marked effect on the storage of the $^{14}C$-lipids in the liver after two hours of digestion (FIG. 6).

On the other hand, they induce a fall, which is not significant because of a high degree of intra group variability, in the quantity of cholesterol which is stored by the liver, decreasing it by 35% and 33%, respectively, as compared with the C group.

In FIG. 6, each histogram is the mean±SEM of the individual values for each group (C: Controls; I: Ingredients; L: Lipogelosomes®). No significant difference was observed when using the Fisher test (p<0.05).

There were no differences between the three groups in the quantities of radiolabelled lipids which were present in the livers at the 24 hour digestion time.

6) Alimentary Lipids and Cholesterol in the Caecum and Faeces

The caeca of the animals which were sacrificed after two hours of digestion either did not contain any $^{14}C$ or $^{3}H$ radioactivity or only contained minute doses of this radioactivity. Furthermore, there were no faeces.

At the 24 hour digestion time (FIG. 7), the quantities of $^{14}C$-lipids found in the caecum and the faeces are significantly increased in the rats which have been given a test meal containing lipogelosomes® (+229.5% as compared with the C group).

The effect is even more pronounced as regards the quantities of alimentary cholesterol, which are significantly increased in the case of both the Ingredients and the LGS groups (+133.3% and +229.4%, respectively, as compared with the C group). The increase in the quantities of cholesterol which is not absorbed by the intestinal mucosa is significantly lower in the I group than in the LGS group.

Figure 7A:
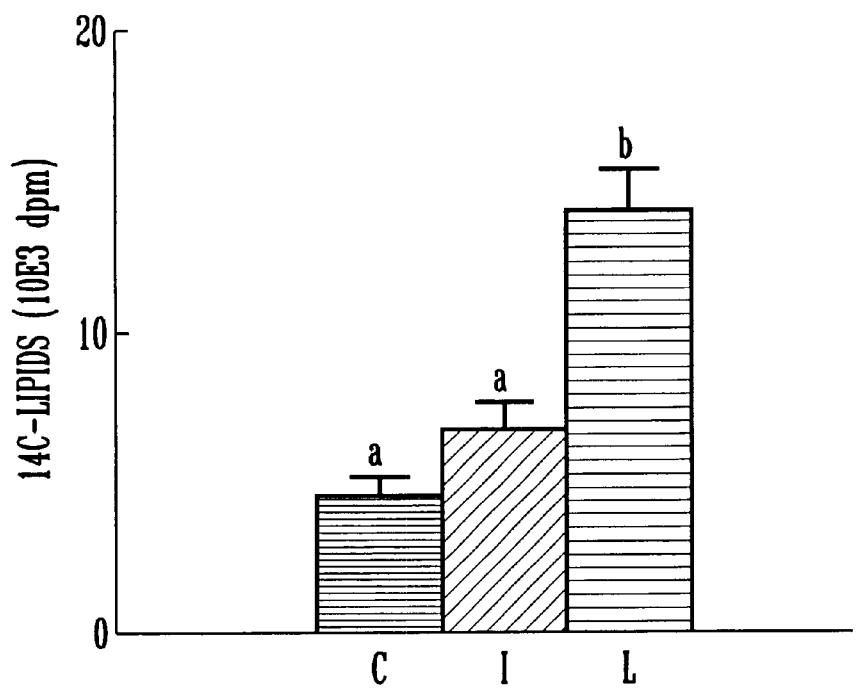
FIG. 7 shows the quantity of radiolabelled lipids (in dpm) which were found in the caecum and faeces of rats which were sacrificed after 24 hours of digestion.
Figure 7B:
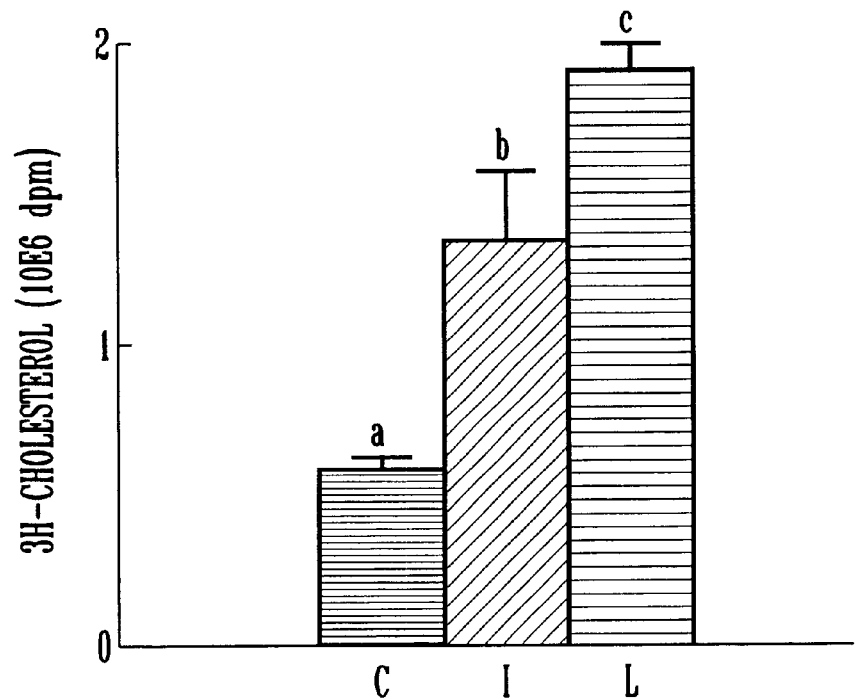

In FIG. 7, each histogram is the mean±SEM of the individual values for each group (C: Controls; I: Ingredients; L: Lipogelosomes®). Different letters indicate significant differences (p<0.01) between the groups as calculated by the Fisher test and the Scheffétest.

This study demonstrates that the ingestion of lipogelosomes® together with the alimentary ration does indeed induce a decrease in the absorption of alimentary lipids (triglycerides and cholesterol). In view of the results, the most plausible hypothesis about the mode of action of the lipogelosomes® is that they induce a reduction in the degree of triglyceride lipolysis in the intestinal lumen, leading to a lower production of monoglycerides and free fatty acids. This fall in lipolysis would have two main consequences: a decrease in the absorption of monoglycerides and free fatty acids; a decrease in the solubilization of cholesterol in the micellar phase, thereby bringing about a reduction in the absorption of cholesterol.

The effect of the lipogelosomes® in decreasing the absorption of cholesterol by the intestinal mucosa is greater than the effect on decreasing the absorption of monoglycerides and free fatty acids. This can be attributed to the fact that the level of cholesterol absorption is much lower than that of triglyceride absorption (80 to 100% and 40 to 60%, respectively).

Thus, the absorption of cholesterol is limited even under "normal" conditions of digestion. The alteration of one parameter (fall in the concentration of monoglycerides and free fatty acids) then leads to a substantial disruption in the absorption of the cholesterol.

Furthermore, it is possible that the lipogelosomes® trap part of the bile salts. The consequence of this effect would be a decrease in the solubilization of cholesterol in the micellar phase, leading to a fall in its absorption.

These results are reinforced by those obtained in the course of a study of the effects of chronic ingestion of lipogelosomes® on lipid metabolism (Example 5 below).

EXAMPLE 5

Effects of the Chronic Ingestion of Different Quantities of LGS on Lipid Metabolism in Rats Animals and Regimes 8 groups of 10 14-week-old Wistar rats (IFFA CREDO, L'Arbresle, France) were constituted randomly.

The animals are caged in an air-conditioned room (21° C. temperature, 50% humidity) having a light-dark cycle of 12 h-12 h. Feed and water were supplied ad libitum.

8 regimes are provided manually. The lipogelosomes® (LGS) and the starting materials constituting the LGSs (I=ingredients) are identical to those in Example 2. The detailed composition of each regime is shown in Table IV. The proportions of the various nutrients in the regimes were calculated taking into account the lipid contributions made by the lipogelosomes® or the ingredients.

8 regimes were tested:

PL—regime which is poor in lipids (4% triglycerides)

RL—regime which is rich in lipids (25% triglycerides +1.2% cholesterol)

LGS 1—regime which is rich in lipids including 1.25% PL (LGS)

LGS 2—regime which is rich in lipids including 2.5% PL (LGS)

LGS 3—regime which is rich in lipids including 3.75% PL (LGS)

I 1—regime which is rich in lipids including 1.25% PL (LGS ingredients)

I 2—regime which is rich in lipids including 2.5% PL (LGS ingredients)

I 3—regime which is rich in lipids including 3.75% PL (LGS ingredients)

In order not to degrade the LGS, LGS regimes 1, 2 and 3 were prepared at the time of use. The other regimes were frozen at −20° C.

TABLE IV

|  | PL | RL | LGS 1 | LGS 2 | LGS 3 | I 1 | I 2 | I 3 |
|---|---|---|---|---|---|---|---|---|
| Casein | 25 | 17 | 17 | 17 | 17 | 17 | 17 | 17 |
| Starch | 35 | 28.8 | 28.8 | 28.8 | 28.8 | 28.8 | 28.8 | 28.8 |
| Glucose | 20 | 11 | 11 | 11 | 11 | 11 | 11 | 11 |
| Maize oil | 3 | 3 | 3 | 3 | 3 | 3 | 3 | 3 |
| Lard | 0 | 22 | 20.75 | 19.5 | 18.25 | 20.75 | 19.5 | 18.25 |
| PL LGS | 0 | 0 | 1.25 | 2.5 | 3.75 | 0 | 0 | 0 |
| Ingredients PL LGS | 0 | 0 | 0 | 0 | 0 | 1.25 | 2.5 | 3.75 |
| Cholesterol | 0 | 1.2 | 1.2 | 1.2 | 1.2 | 1.2 | 1.2 | 1.2 |
| Cellulose | 9 | 9 | 9 | 9 | 9 | 9 | 9 | 9 |
| Vitamins | 1 | 1 | 1 | 1 | 1 | 1 | 1 | 1 |
| Minerals | 7 | 7 | 7 | 7 | 7 | 7 | 7 | 7 |
| Energy (Kcal/100 g) | 347 | 452.2 | 452.2 | 452.2 | 452.2 | 452.2 | 452.2 | 452.2 |

Compositions of the regimes (g/100).
PL = regime which is poor in lipids (3%);
RL = regime which is rich in lipids (25%);
LGS 1 = regime which contains 25% lipids including 1.25% phospholipids in the form of lipogelosomes ®;
LGS 2 = regime which contains 25% lipids including 2.5% phospholipids in the form of lipogelosomes ®;
LGS 3 = regime which contains 25% lipids including 3.75% phospholipids in the form of lipogelosomes ®;
I 1 = regime which contains 25% lipids including 1.25% phospholipids;
I 2 = regime which contains 25% lipids including 2.5% phospholipids;
I 3 = regime which contains 25% lipids including 3.75% phospholipids.

COURSE OF THE STUDY:

The weights of the rats are measured at the beginning and the end of the study.

The quantity ingested is measured (over 3 days) after 2 weeks and at the end of the study.

Blood samples are taken from the RL and LGS 3 groups at the beginning of the study and after 3 weeks of the regime.

The faeces were collected (over 4 days) during the pen-ultimate week; they were weighed and frozen at −20° C.

The coefficient of absorption of the cholesterol is measured on the faeces which are collected at the beginning of the last week.

After 6 weeks of the regime, the animals are sacrificed under anaesthesia after a day of fasting: the liver (weight taken and then frozen at −20° C.) and approximately 10 ml of blood (puncture of the abdominal aorta) were removed. The serum is obtained by centrifuging the whole blood.

All the analyses on sera are carried out on fresh serum.

ANALYSES

The triglycerides (G. BUCCOLO et al., Clin. Chem., 1973, 19, 476–482), the phospholipids (M. TAKAYAMA et al., Clin. Chem. Acta., 1977, 79, 93–98) the total cholesterol (J. SIEDEL et al., Clin. Chem., 1983, 29, 1075–1080) and the free cholesterol (F. STAHLER et al., Med. Lag., 1973, 30, 29–37) were assayed in 20 rats (RL and LGS 3 groups) at the starting time and after 3 weeks of the regime, using enzymic-colorimetric methods.

The triglycerides, phospholiplds, total cholesterol and free cholesterol in the serum of each rat were assayed after 6 weeks of the regime, using the same methods.

The VLDL (very low density lipoproteins), LDL (low density lipoproteins) and HDL (high density lipoproteins) in the serum of each rat were separated (T. BROUSSEAU et al., Clin. Chem., 1993, 39, 960–964), at the end of the study, by means of sequential ultracentrifugation (VLDL: 436,000 g, 2.5 h at 10° C.; LDL: 436,000 g, 2.5 h at 10° C.; HDL: 436,000 g, 5 h at 10° C.) using a Beckman Optima TLX ultracentrifuge and the TL—100.2 rotor. The triglycerides, the phospholipids, the total cholesterol and the free cholesterol were assayed on the different classes of lipoproteins using the abovementioned enzymic-colorimetric methods.

The g-GT (J. P. PRESIJN et al., J. Clin. Chem. Biochem., 1976, 14, 421–427), GOT (G. KESSLER et al., 9th Int. Congr. Clin. Chem., Toronto, 1975), GPT (G. KESSLER et al., 9th Int. Congr. Clin. Chem., Toronto, 1975) and alkaline phosphatase (S. MORGENSTERN et al., Clin. Chem., 1965, 11, 876–881) toxicological enzymic activities were assayed on the sera of the RL and LGS 3 groups at the starting time and after 3 weeks on the regime, and on the serum of each rat at the end of 6 weeks of the regime.

Approximately 1 g of the liver from each rat was ground in ethanol. The triglycerides (G. BUCCOLO et al., Clin. Chem., 1973, 19, 476–482) and the phospholipids (J. AMIC et al., Clin. Chem. Acta., 1972, 40, 107–114) were assayed after extraction using the Folch method (J. FOLCH et al., J. Biol. Chem., 1957, 226, 498–509). The total cholesterol (J. SIEDEL et al., Clin. Chem., 1983, 29, 1075–1080) was assayed after saponification, extraction with petroleum ether, washing with ethanol/water, evaporating and dissolving in isopropanol (L. CARA et al., Nutr. Res., 1991, 11, 907–916).

Aliquots (specific preparations) of the liver from each rat were prepared in order to preserve samples, by freezing at −80° C., for possible future analyses (HMGCoA red., ACAT, 7 a hydroxylase).

RESULTS

Change in Weight and Quantity Ingested

At the beginning of the study, the means of the weights of each group of rats were not significantly different (from 325±2 g to 330±2 g). After 6 weeks of the regime, the weights of the rats in groups I 1 (419±7 g) and I 3 (414±9 g) were significantly lower than the weights of the LGS 3 group (444±7 g).

By contrast, no significant difference was apparent between the LGS and I groups and the control RL regime (425±8 g). The same significant differences appeared with regard to the gain in weight (RL: 95±9 g, LGS 3: 116±9 G, I 1: 92±7 G, I 3: 89±9 g).

After 2 weeks and 5 weeks, the values of the quantity ingested by the PL group (41.2±1.5 g and 38.9±0.9 g, respectively) were significantly higher than the values for the quantity ingested by the other groups (from 25.3±1.0 g to 31.7±1.0 g). Since the PL regime contained fewer calories per gram of the regime, the rats in this group increased the quantities they ingested.

The quantities of LGS ingested (in powder form) were as follows: LGS 1: 0.51 g/d; LGS 2: 1.04 g/d; LGS 3: 1.67 g/d, which corresponds to the following quantities of phospholipids: LGS 1: 0.28 g/d; LGS 2: 0.57 g/d; LGS 3: 0.92 g/d.

Variations in the Serum Lipid Parameters

Table V shows the serum parameter values for the rats after 6 weeks of the regime.

TABLE V

|  | PL | RL | LGS 1 | LGS 2 | LGS 3 | I 1 | I 2 | I 3 |
|---|---|---|---|---|---|---|---|---|
| Triglycerides (mM) | $1.83 \pm 0.21^a$<br>$1.62 \pm 0.18^a$ | $0.48 \pm 0.04^b$<br>$0.37 \pm 0.04^{bcd}$ | $0.48 \pm 0.04^b$<br>$0.32 \pm 0.04^{bcd}$ | $0.64 \pm 0.06^{bc}$<br>$0.46 \pm 0.06^d$ | $0.68 \pm 0.06^{bc}$<br>$0.42 \pm 0.05^{bd}$ | $0.45 \pm 0.03^b$<br>$0.24 \pm 0.02^{bc}$ | $0.82 \pm 0.09^c$<br>$0.44 \pm 0.04^{bd}$ | $0.47 \pm 0.03^b$<br>$0.20 \pm 0.04^c$ |
| Phospholipids (mM) | $1.82 \pm 0.08^a$ | $1.24 \pm 0.07^b$ | $1.41 \pm 0.07^{bc}$ | $1.33 \pm 0.05^{bc}$ | $1.26 \pm 0.07^{bc}$ | $1.34 \pm 0.03^{bc}$ | $1.42 \pm 0.06^c$ | $1.28 \pm 0.05^{bc}$ |
| Total cholesterol (mM) | $1.91 \pm 0.08^{ab}$<br>$2.05 \pm 0.09^{bc}$ | $2.02 \pm 0.22^{bc}$<br>$2.12 \pm 0.24^{bc}$ | $2.07 \pm 0.11^b$<br>$2.10 \pm 0.12^{bc}$ | $1.82 \pm 0.11^{ab}$<br>$1.80 \pm 0.11^{ab}$ | $1.57 \pm 0.12^a$<br>$1.53 \pm 0.12^a$ | $2.29 \pm 0.16^c$<br>$2.40 \pm 0.18^c$ | $1.81 \pm 0.09^{ab}$<br>$1.95 \pm 0.09^b$ | $1.80 \pm 0.06^{ab}$<br>$1.99 \pm 0.07^b$ |
| Free cholesterol (mM) | $0.28 \pm 0.03^a$<br>$0.33 \pm 0.03^b$ | $0.28 \pm 0.05^a$<br>$0.31^{0.05b}$ | $0.26 \pm 0.02^a$<br>$0.30 \pm 0.03^b$ | $0.22 \pm 0.03^{ab}$<br>$0.24 \pm 0.03^{bc}$ | $0.17 \pm 0.02^b$<br>$0.16 \pm 0.02^c$ | $0.27 \pm 0.03^a$<br>$0.27 \pm 0.03^{bc}$ | $0.22 \pm 0.02^{ab}$<br>$0.29 \pm 0.04^b$ | $0.26 \pm 0.02^a$<br>$0.44 \pm 0.06^a$ |
| Esterified cholesterol (mM) | $1.63 \pm 0.07^{ab}$<br>$1.70 \pm 0.06^{ab}$ | $1.74 \pm 0.18^{bc}$<br>$1.81 \pm 0.20^{bc}$ | $1.81 \pm 0.10^{bc}$<br>$1.81 \pm 0.11^{bc}$ | $1.60 \pm 0.08^{ab}$<br>$1.58 \pm 0.09^{ab}$ | $1.40 \pm 0.10^a$<br>$1.36 \pm 0.11^a$ | $2.02 \pm 0.13^c$<br>$2.14 \pm 0.16^c$ | $1.60 \pm 0.09^{ab}$<br>$1.68 \pm 0.09^{ab}$ | $1.54 \pm 0.06^{ab}$<br>$1.55 \pm 0.09^{ab}$ |
| Alc. Ph. (U/I) | $78.8 \pm 4.9^{ab}$ | $88.8 \pm 8.1^b$ | $89.4 \pm 6.0^b$ | $78.3 \pm 4.0^{ab}$ | $81.4 \pm 5.0^{ab}$ | $71.2 \pm 4.0^a$ | $88.4 \pm 4.5^b$ | $80.1 \pm 3.4^{ab}$ |
| GOT (U/I) | $134 \pm 10^{ac}$ | $206 \pm 39^b$ | $186 \pm 20^{ab}$ | $149 \pm 19^{abc}$ | $109 \pm 9^c$ | $152 \pm 20^{abc}$ | $155 \pm 18^{abc}$ | $144 \pm 13^{ac}$ |
| GPT (U/I) | $26.7 \pm 2.4^a$ | $74.9 \pm 36.1^b$ | $67.4 \pm 14.7^{ab}$ | $48.1 \pm 13.6^{ab}$ | $30.9 \pm 5.4^{ab}$ | $58.9 \pm 14.3^{ab}$ | $54.4 \pm 14.9^{ab}$ | $29.9 \pm 3.3^{ab}$ |
| g-GT (U/I) | $0.30 \pm 0.21$ | $0.00 \pm 0.00$ | $0.00 \pm 0.00$ | $0.50 \pm 0.22$ | $0.00 \pm 0.00$ | $0.00 \pm 0.00$ | $0.40 \pm 0.22$ | $0.60 \pm 0.60$ |

The values represent the mean ± SEM for 10 rats.
For a given parameter, different letters indicate significant differences.
For a given parameter, two lines of values indicate that the assays were carried out in two different laboratories.
PL = regime which is poor in lipids (3%);
RL = regime which is rich in lipids (25%);
LGS 1 = regime which contains 25% lipids including 1.25% phospholipids in the form of lipogelosomes ®;
LGS 2 = regime which contains 25% lipids including 2.5% phospholipids in the form of lipogelosomes ®;
LGS 3 = regime which contains 25% lipids including 3.75% phospholipids in the form of lipogelosomes ®;
I 1 = regime which contains 25% lipids including 1.25% phospholipids;
I 2 = regime which contains 25% lipids including 2.5% phospholipids;
I 3 = regime which contains 25% lipids including 3.75% phospholipids The ingestion of the lipid-rich regimes induced a significant decrease in the serum triglycerides of the rats as compared with the regime which is poor in alimentary lipids (Table V). While this result has been found in other studies (JL. VIGNE et al., Br. J. Nutr., 1987, 58, 405–413; F. CHANUSSOT et al., Ann. Nutr. Metab., 1988, 32, 271–281; G. NALBONE et al., J. Nutr., 1988, 118, 809–817; G. NALBONE et al., Lipids., 1989, 24, 179–186), the amplitude of the variations depends on the composition of the regimes, on the rat strain and on the duration of the regimes. The I 2 regime induced a significant increase in the serum triglycerides as compared with the RL, LGS 1, I 1 and I 3 regimes.

The analysis of the lipids of the different classes of lipoproteins (Table VI) shows that the increase in triglyceridaemia obtained using the PL regime was due primarily to a significant increase in the VLDL triglycerides and secondarily to a significant increase in the LDL and HDI triglycerides. The increase obtained with the I 2 regime is mainly due to an increase in the VLDL triglycerides. As compared with the RL regime, the LGS 3 regime induced a significant increase in the LDL triglycerides; the LGS 2, I 2 and I 3 regimes brought about a significant increase in the HDL triglycerides. Increasing the quantity of LGS or I ingested only induced slight variations in the triglycerides in the different classes of lipoproteins: no dose effect is therefore apparent in the case of this parameter.

TABLE VI

Lipid composition of the lipoproteins after 6 weeks of the regime

|  | TOTAL CHOLESTEROL (mM) | | | FREE CHOLESTEROL (mM) | | | ESTERIFIED CHOLESTEROL (mM) | | | TRIGLYCERIDES (mM) | | | PHOSPHOLIPIDS (mM) | | |
|---|---|---|---|---|---|---|---|---|---|---|---|---|---|---|---|
|  | VLDL | LDL | HDL | VLDL | LDL | HDL | VLDL | LDL | HDL | VLDL | LDL | HDL | LDL | LDL | HDL |
| PL | $0.22^a$<br>$\pm 0.03$ | $0.54^{abc}$<br>$\pm 0.05$ | $1.15^a$<br>$\pm 0.04$ | $0.06^{ab}$<br>$\pm 0.02$ | $0.02^a$<br>$\pm 0.01$ | $0.19^a$<br>$\pm 0.01$ | $0.16^a$<br>$\pm 0.02$ | $0.52^{ac}$<br>$\pm 0.05$ | $0.96^a$<br>$\pm 0.04$ | $1.03^a$<br>$\pm 0.16$ | $0.13^a$<br>$\pm 0.02$ | $0.67^a$<br>$\pm 0.06$ | $0.31^{ade}$<br>$\pm 0.04$ | $0.51^a$<br>$\pm 0.03$ | $0.99^a$<br>$\pm 0.04$ |
| RL | $0.66^b$<br>$\pm 0.10$ | $0.55^{ab}$<br>$\pm 0.12$ | $0.81^{bdf}$<br>$\pm 0.04$ | $0.10^b$<br>$\pm 0.02$ | $0.07^{cd}$<br>$\pm 0.04$ | $0.11^{bc}$<br>$\pm 0.02$ | $0.56^b$<br>$\pm 0.08$ | $0.48^{abcd}$<br>$\pm 0.09$ | $0.70^{bcd}$<br>$\pm 0.04$ | $0.28^{bcde}$<br>$\pm 0.03$ | $0.07^{bcd}$<br>$\pm 0.01$ | $0.14^b$<br>$\pm 0.01$ | $0.26^{abce}$<br>$\pm 0.02$ | $0.38^{bc}$<br>$\pm 0.05$ | $0.61^{bc}$<br>$\pm 0.03$ |
| LGS 1 | $0.42^d$<br>$\pm 0.06$ | $0.71^{ac}$<br>$\pm 0.07$ | $0.94^{bce}$<br>$\pm 0.06$ | $0.06^{ad}$<br>$\pm 0.01$ | $0.07^{cd}$<br>$\pm 0.01$ | $0.14^{bc}$<br>$\pm 0.02$ | $0.36^c$<br>$\pm 0.05$ | $0.64^c$<br>$\pm 0.05$ | $0.80^c$<br>$\pm 0.04$ | $0.26^{bce}$<br>$\pm 0.03$ | $0.05^b$<br>$\pm 0.01$ | $0.17^{bc}$<br>$\pm 0.01$ | $0.23^{bce}$<br>$\pm 0.02$ | $0.43^{ac}$<br>$\pm 0.03$ | $0.75^d$<br>$\pm 0.05$ |
| LGS 2 | $0.36^{ad}$<br>$\pm 0.04$ | $0.50^{abc}$<br>$\pm 0.08$ | $0.96^{ce}$<br>$\pm 0.05$ | $0.3^{acd}$<br>$\pm 0.01$ | $0.03^{ac}$<br>$\pm 0.02$ | $0.16^{ab}$<br>$\pm 0.01$ | $0.33^c$<br>$\pm 0.03$ | $0.47^{ab}$<br>$\pm 0.06$ | $0.80^c$<br>$\pm 0.04$ | $0.35^{bcde}$<br>$\pm 0.04$ | $0.08^{ce}$<br>$\pm 0.01$ | $0.22^{cd}$<br>$\pm 0.02$ | $0.21^{bc}$<br>$\pm 0.02$ | $0.38^{bc}$<br>$\pm 0.03$ | $0.74^d$<br>$\pm 0.03$ |

TABLE VI-continued

Lipid composition of the lipoproteins after 6 weeks of the regime

|  | TOTAL CHOLESTEROL (mM) | | | FREE CHOLESTEROL (mM) | | | ESTERIFIED CHOLESTEROL (mM) | | | TRIGLYCERIDES (mM) | | | PHOSPHOLIPIDS (mM) | | |
|---|---|---|---|---|---|---|---|---|---|---|---|---|---|---|---|
|  | VLDL | LDL | HDL | VLDL | LDL | HDL | VLDL | LDL | HDL | VLDL | LDL | HDL | LDL | LDL | HDL |
| LGS 3 | $0.37^{ad}$ ±0.05 | $0.40^{b}$ ±0.07 | $0.80^{df}$ ±0.06 | $0.02^{c}$ ±0.01 | $0.01^{ab}$ ±0.01 | $0.14^{bc}$ ±0.01 | $0.35^{c}$ ±0.04 | $0.39^{cd}$ ±0.06 | $0.66^{b}$ ±0.04 | $0.38^{bcd}$ ±0.04 | $0.10^{c}$ ±0.01 | $0.20^{bcd}$ ±0.02 | $0.21^{bc}$ ±0.02 | $0.36^{bc}$ ±0.03 | $0.69^{bd}$ ±0.05 |
| I 1 | $0.93^{c}$ ±0.11 | $0.65^{c}$ ±0.09 | $0.70^{f}$ ±0.02 | $0.07^{bd}$ ±0.01 | $0.10^{d}$ ±0.01 | $0.10^{c}$ ±0.01 | $0.86^{d}$ ±0.10 | $0.55^{ac}$ ±0.08 | $0.60^{b}$ ±0.02 | $0.24^{cb}$ ±0.02 | $0.08^{ce}$ ±0.01 | $0.13^{b}$ ±0.01 | $0.32^{d}$ ±0.02 | $0.50^{a}$ ±0.02 | $0.53^{c}$ ±0.02 |
| I 2 | $0.47^{d}$ ±0.03 | $0.49^{ab}$ ±0.06 | $0.86^{bcd}$ ±0.03 | $0.03^{acd}$ ±0.01 | $0.02^{ac}$ ±0.01 | $0.16^{ab}$ ±0.03 | $0.44^{bc}$ ±0.02 | $0.47^{abcd}$ ±0.05 | $0.70^{bcd}$ ±0.03 | $0.46^{d}$ ±0.05 | $0.09^{de}$ ±0.01 | $0.26^{d}$ ±0.03 | $0.28^{de}$ ±0.01 | $0.42^{ac}$ ±0.03 | $0.72^{d}$ ±0.03 |
| I 3 | $0.42^{d}$ ±0.04 | $0.36^{b}$ ±0.06 | $1.02^{ae}$ ±0.06 | $0.03^{ac}$ ±0.01 | $0.03^{ac}$ ±0.01 | $0.21^{a}$ ±0.02 | $0.39^{c}$ ±0.03 | $0.33^{d}$ ±0.05 | $0.81^{c}$ ±0.06 | $0.19^{c}$ ±0.02 | $0.06^{bc}$ ±0.01 | $0.22^{cd}$ ±0.01 | $0.20^{c}$ ±0.02 | $0.30^{b}$ ±0.03 | $0.78^{d}$ ±0.04 |

Legend to Table VI:
The values represent the mean ±SEM (in italics) for 10 rats. For each column, different letters (written as exponents) indicate significant differences.
VLDL = Very Low Density Lipoproteins; LDL = Low Density Lipoproteins; HDL = High Density Lipoproteins; PL = regime which is poor in lipids (3%); RL = regime which is rich in lipids (25%); LGS 1 = regime which contains 25% lipids including 1.25% phospholipids in the form of lipogelosomes ®; LGS 2 = regime which contains 25% lipids including 2.5% phospholipids in the form of lipogelosomes®; LGS 3 = regime which contains 25% lipids including 3.75% phospholipids in the form of lipogelosomes®; I 1 = regime which contains 25% lipids including 1.25% phospholipids; I 2 = regime which contains 25% lipids including 2.5% phospholipids; I 3 = regime which contains 25% lipids including 3.75% phospholipids.

With regard to the phospholipids in the serum (Table V), the lipid-poor regime also induced a significant increase in this parameter as compared with the lipid-rich regimes. Only the I 2 regime brought about an increase in serum phospholipids as compared with the RL regime.

After the different classes of lipoproteins had been separated (Table VI), it was observed that the increase in phospholipids in the PL group was essentially due to a quantitative increase in the HDL phospholipids. Since this class of lipoprotein contains most phospholipids, it is natural for the increase to be found at this level. As regards the effects caused by LGS and I, the LGS 1, LGS 2, I 2 and I 3 regimes were observed to bring about a significant increase in HDL phospholipids as compared with the RL group.

The RL regime induced a slight increase in the total cholesterol present in the serum as compared with the PL regime (Table V). As compared with the RL regime, the LGS 3 regime was observed to bring about a significant decrease (−22.3%) in the total cholesterol in the serum. A smaller decrease was obtained with the I 3 regime (−10.9%).

Table VI shows that the decrease in total cholesterol obtained with the LGS 3 regime is due to a significant decrease in the total cholesterol present in the VLDL and, secondarily, to a tendency for the total cholesterol in the LDL to decrease. As compared with the RL regime, the total cholesterol in the VLDL+LDL decreased by 36.4% following ingestion of the LGS 3 regime. By contrast, no variation in the total cholesterol in the HDL was noted following the ingestion of this regime.

The effects of the alimentary phospholipids which are observed in the animal also depend on the methodology employed. If the effects of the LGS 3 and I 3 regimes are compared, it is important to note that the LGS 3 regime induced a decrease in the cholesterolaemia which was twice as great. On the other hand, these effects of the LGS on cholesterolaemia are a function of the dose ingested.

Increasing the quantity of alimentary lipids ingested did not induce any significant variation (apart from the case of the LGS 3 regime) in free cholesterol in the serum (Table V).

Only the LGS 3 regime induced a significant decrease of 39% in free cholesterol in the serum as compared with the RL regime.

By contrast, the results obtained with regard to the lipids in the different classes of lipoproteins (Table VI) show that the distribution of free cholesterol differs in accordance with the regime ingested.

The decrease in free cholesterol in the serum which follows the LGS 3 regime, as compared with the RL regime, is due to a significant decrease in the free cholesterol in the VLDL and the LDL. It also has to be mentioned that the I 3 regime induced a significant increase, as compared with the RL regime, in free cholesterol in the HDL.

With regard to the variations in esterified cholesterol in the serum (Table V), a significant decrease of 20% was observed following ingestion of the LGS 3 regime, as compared with the RL regime. While the LGS 2, I 2 and I 3 regimes have a tendency to induce a decrease in this parameter, this decrease is not significant.

In the case of the LGS 3 regime, the decrease as compared with the RL regime is due to a significant decrease in the esterified cholesterol in the VLDL and to a tendency for this parameter to decrease at the level of the LDL and the HDL (Table VI). Still as compared with the RL regime, we did not observe any significant variation in the esterified cholesterol in the LDL and HDL when using the regimes containing LGS or I.

Table V (continued) presents the results which were obtained with regard to toxicological parameters in the sera of the rats after 6 weeks of the dietary regime. As compared with the PL regime, the addition of lipids to the regimes did not induce any increase in alkaline phosphatase. On the other hand, the I 1 regime induced a significant decrease in this parameter as compared with the RL, LGS 1 and I 2 regimes.

The RL regime significantly increased GOT activity as compared with the PL regime.

The other regimes did not significantly alter the activity of this transaminase as compared with the PL regime. On the other hand, a substantial significant decrease (47%) was noted with the LGS 3 regime as compared with the RL regime. A significant decrease (30%) was also obtained with the I 3 regime.

As compared with the PL regime, the RL regime induced an increase in GPT activity.

The regimes containing LGS or I did not significantly alter the activity of this transaminase as compared with the PL and RL regimes. In this case, too, the lowest values were obtained following ingestion of the LGS 3 and I 3 regimes.

As far as g-GT activity was concerned, the sensitivity of the assay method was insufficient for measuring this enzyme activity, given that the values were too low. No activity was detected for this enzyme whatever the regime ingested.

The results of the toxicological assays show that the ingestion of LGS at these doses is not toxic in rats. The LGS even have a tendency to exhibit a hepato-protective effect.

Changes in the Lipid Parameters in the Livers

The addition of alimentary lipids to the regimes induces a significant increase in the weights of the livers, whereas increasing the quantity of LGS tends to decrease the liver weights. This variation is more pronounced when the quantity of ingredients (group I) is increased. It has to be recalled that the weights of the rats were lower in the case of the I groups. It is therefore normal for the weights of the livers to be lower in these groups.

In this study, the ingestion of LGS did not induce any significant variation in the weights of the livers.

However, the results which were obtained demonstrate that the lipogelosomes have different effects from those produced by the ingredients.

CONCLUSION

This study demonstrates several important results:

The quantities of LGS employed (from 1.25 to 3.75% in the regimes) are not toxic.

Metabolic effects are obtained in the rat when using 3.75% phospholipid in the form of LGS in the regimes (ratio of alimentary triglycerides to phospholipids of: TG/PL=5.7). The 2.5% dose produces effects which are less pronounced (TG/PL=9).

Given that the rat possesses a well-regulated lipid metabolism, it is probable that effects would be observed in humans when using 2.5% doses. If we consider that a human

TABLE VII

Weights and lipids contents of the livers of the rats after 6 weeks of the regime

|  | PL | RL | LGS 1 | LGS 2 | LGS 3 | I 1 | I 2 | I 3 |
|---|---|---|---|---|---|---|---|---|
| Weights of the livers (g) | $10.8 \pm 0.3^a$ | $14.1 \pm 0.5^{bt}$ | $14.1 \pm 0.9^{bd}$ | $13.3 \pm 0.4^{bcdt}$ | $13.5 \pm 0.5^{bcdt}$ | $12.6 \pm 0.2^{ce}$ | $12.6 \pm 0.6^{et}$ | $11.4 \pm 0.5^a$ |
| Total cholesterol (mg/g of liver) | $3.7 \pm 0.3^a$ | $17.3 \pm 2.4^b$ | $22.5 \pm 2.3^{bc}$ | $22.0 \pm 2.5^{bc}$ | $26.0 \pm 1.4^{cd}$ | $36.7 \pm 2.5^d$ | $33.4 \pm 2.7^d$ | $24.7 \pm 1.1^c$ |
| Total cholesterol (mg/1liver) | $39 \pm 3^a$ | $244 \pm 36^b$ | $317 \pm 38^{bc}$ | $299 \pm 41^{bc}$ | $352 \pm 24^{ce}$ | $461 \pm 32^d$ | $429 \pm 45^{de}$ | $283 \pm 18^{bc}$ |
| Triglycerides (mg/g of liver) | $13.2 \pm 0.7^a$ | $18.7 \pm 1.3^b$ | $30.5 \pm 2.6^{de}$ | $27.1 \pm 1.7^{cd}$ | $38.9 \pm 2.2^f$ | $26.2 \pm 1.7^{cd}$ | $34.3 \pm 1.6^{ef}$ | $23.9 \pm 1.5^c$ |
| Triglycerides mg/liver) | $142 \pm 8^a$ | $260 \pm 15^b$ | $437 \pm 54^{de}$ | $365 \pm 32^{cd}$ | $528 \pm 41^e$ | $328 \pm 22^{bc}$ | '$439 \pm 35^{de}$ | $277 \pm 25^{bc}$ |

The values represent the mean ± SEM for 10 rats. For a given parameter, different letters indicate significant differences. PL = regime which is poor in lipids (3%); RL = regime which is rich in lipids (25%); LGS 1 = regime which contains 25% of lipids including 1.25% phospholipids in the form of lipogelosomes ®; LGS 2 = regime which contains 25% lipids including 2.5% phospholipids in the form of lipogelosomes ®; LGS 3 = regime which contains 25% lipids including 3.75% phospholipids in the form of lipogelosomes ®; I 1 = regime which contains 25% lipids including 1.25% phospholipids; I 2 = regime which contains 25% lipids including 2.5% phospholipids; I 3 = regime which contains 25% lipids including 3.75% phospholipids.

As regards total cholesterol in the livers, the addition of lipids to the alimentary regimes induces a significant increase in the concentration (mg/g of liver) and in the total quantity (mg/liver) of total cholesterol in the livers (Table VII). As compared with the RL regime, the concentration of total cholesterol was increased significantly when using the LGS 3 regime and the three I regimes. On the other hand, the total quantity of cholesterol in the livers is no longer significant in the case of the I 3 regime whereas the significant differences as compared with the RL regime are unchanged in the case of the other groups.

Increasing the quantity of alimentary lipids induced a significant increase in the concentration and the total quantity of triglycerides in the livers (Table VII). As compared with the RL regime, the addition of LGS or I increased the concentration (mg/g of liver) of triglycerides in the livers. On the other hand, given that the liver weights differed depending on the groups, we no longer observed any significant difference with regard to the quantity (mg/liver) of triglycerides in the livers in the case of the I 1 and I 3 groups.

The effects of different quantities of LGS or I on the lipid parameters in the livers do not correlate with the quantity ingested.

being ingests approximately 100 g of triglycerides per day, it would be necessary to ingest approximately 11 g of phospholipids in the form of LGS in order to have a hope of observing effects (that is 20 g of LGS if the LGS contain 55% phospholipids).

The main effects of the LGS are observed at the level of the plasma cholesterol and are a function of the dose ingested (total cholesterol: correlation coefficient R=0.91; free cholesterol: R=0.98; esterified cholesterol: R=0.88). The decreases relate principally to the VLDL and the LDL.

Some of the effects induced by the LGS on the metabolism of the lipids can be compared with those induced by cholestyramine.

Table VIII below shows the effects exerted by the LGS on bile salts and sterols.

TABLE VIII

| Daily faecal excretion | Daily faecal excretion of | Daily faecal excretion | Ratio of primary bile acids/ | Ratio of primary neutral sterols/ |
|---|---|---|---|---|

| Groups | of bile acids mg/d* | neutral sterols mg/d* | of total lipids mg/d* | secondary bile acids* | secondary neutral sterols* |
|---|---|---|---|---|---|
| C | 32.2 ± 1.5 | 218.1 ± 9.0 | 978.7 ± 54.0 | 1.19 ± 0.17 | 11.41 ± 1.01 |
| R1 | | | | | |
| LGS3 | 26.7 ± 2.0[a] | 295.7 ± 8.8[c] | 835.6 ± 37.4[a] | 0.60 ± 0.10[b] | 1.27 ± 0.23[c] |
| R41 | | | | | |

*mean ± SEM for 10 rats, [a], [b] and [c] differ significantly from the preceding row at $p < 0.05$, $p < 0.008$ and $p < 0.001$, respectively.

Taken overall, the results of this study demonstrate that the LGS surprisingly exhibit the following properties:

Effects on Lipid Metabolism

Decrease in total cholesterol (Table V) between the control regime (RL) and the highest dose of LGS (LGS 3).

More precisely, the LGS 3 bring about a significant decrease in total plasma cholesterol of the order of 22% and in esterified cholesterol of the order of 20%. These decreases are dose-dependant. Furthermore, the LGS 3 bring about a decrease in the total cholesterol in the VDL of the order of 44% and in the total cholesterol in the LDL of the order of 36%.

The LGS induce a favourable distribution of the lipids in different classes of lipoproteins (Table VI).

Absence of Toxicity and Hypotoxic Effect

When using LGS 3, a decrease in GOT (continuation of Table V), as compared with the control (RL), and a tendency for GPT to decrease.

Effective Dose by the Oral Route between 2.5 and 3.75% phospholipids in the regime.

Decrease in the primary bile salts/secondary bile salts and primary neutral sterols/secondary neutral sterols ratios (Table VIII); these results indicate a change in the quantity and/or quality of the intestinal bacteria in the presence of LGS.

An increase in the faecal excretion of neutral sterols of the order of +36% is observed when using LGS 3, while there is a decrease in faecal bile acids of the order of −17%.

EXAMPLE 6

Qualitative and quantitative comparison of the dispersion of lipogelosomes® in aqueous phase which is obtained in step 1 of the process according to Example 2, as compared with an aqueous solution which is reconstituted from a pulverulent composition which is obtained in step 2 in accordance with Example 2.

TABLE IX

| | LGS dispersion | Reconstituted solution | Difference |
|---|---|---|---|
| [PL] in g/g of dry matter | 0.359 ± 0.020 | 0.341 ± 0.017 | −5.0% (NS) |
| [Gelatinizing agent] in g/g of dry matter | 0.344 ± 0.028 | 0.315 ± 0.014 | −8.4% (NS) |
| [Gelatinizing agent]/[PL] | 1.04 | 1.08 | +3.8% (NS) |
| Change in the lipid profile | NO | NO | — |
| Ø in nm | 183 ± 3 | 180 ± 27 | −1.6% (NS) |
| Polydispersity in % | | | |
| Microscopic appearance | 40.9 ± 2.2 spherical vesicles | 41.7 ± 2.1 retracted vesicles | +2.0% (NS) YES |

[PL] = concentration of phospholipids (Biomérieux enzyme kit); [gelatinizing agent] = concentration of total gelatinizing agent (Lowry colorimetric method); change in lipid profile: according to HPLC carried out on the PL; Ø number and polydispersity: in accordance with SCP granulometry; electron-microscopic appearance: photographic observations (negative staining electron microscopy); (NS) = not significant.

Thus, as is evident from the above, the invention is in no way limited to those of its embodiments and modes of application which have just been described more explicitly; on the contrary, it encompasses all the variants of these embodiments of which the skilled person can conceive without departing from the context or the scope of the present invention.

What is claimed is:

1. A pulverulent composition, which comprises unilamellar liposomes, said liposomes, comprising:
    a) an external lipid phase which consists essentially of phospholipids; and
    b) an internal aqueous nucleus forming a temperature-reversible aqueous gel which radiates out up to the external lipid phase, which internal aqueous nucleus consists essentially of a mixture M of at least two different non-polymerizable gelatinizing agents G1 and G2, whose gel-sol phase transition point is higher than or equal to 37° C., with G1 being a gelatinizing agent which is selected from the group consisting of gelatin and carrageenans, and G2 being selected from the group consisting of carrageenans whose properties are different from the carrageenans selected for G1, and celluloses;
    which liposomes have a diameter of between 20 nm and 200 nm;
    and wherein the pulverulent composition is present in the form of particulate units which have a mean diameter of between 10 μm and 1000 μm and which are formed from one or more of the liposomes which is/are surrounded by a matrix which is selected from the group consisting of a dehydrated temperature-reversible aqueous gel which is selected from the group consisting of gelatin, carrageenans, dextrins and mixtures thereof, such that it contains, on average, from $10^{16}$ to $10^{18}$ liposomes/g of powder.

2. The pulverulent composition of claim 1, wherein the said internal aqueous nucleus of the liposomes additionally contains at least one glycosidic stabilizing agent or at least one agent for regulating the osmolarity of the medium or at least one surface-active agent or a combination thereof.

3. The pulverulent composition of claim 1, which comprises, in % (m/m):
    from 25 to 75% of phospholipids, from 5 to 45% of gelatinizing agents, from 0 to 70% of glycosidic stabilizing agent, from 0 to 15% of agent for regulating the osmolarity of the medium, from 0 to 20% of surface-active agents and from 0 to 15% of dextrins.

4. The pulverulent composition of claim 1, which comprises from 70 to 95% of gelatinizing agent G1 and from 5 to 30% of gelatinizing agent G2.

5. The pulverulent composition of claim 1, wherein the glycosidic stabilizing agent is sucrose or trehalose.

6. The pulverulent composition of claim 1, wherein the lipids which constitute the external phospholipid phase of the liposomes comprise from 20 to 25% of phosphatidylcholine, from 10 to 18% of phosphatidylethanolamine, and from 9 to 15% of phosphatidylinositol.

7. The pulverulent composition of claim 1, wherein the lipids which constitute the external phospholipid phase of the said liposomes comprise purified phospholipids, either on their own or in a mixture.

8. A process for preparing the pulverulent composition of claim 1, in which the external matrix of the particulate units comprises a dehydrated, temperature-reversible, aqueous gel fraction, said process comprising:

(1) preparing a dispersion of liposomes having a gelatinized internal nucleus in aqueous phase by:
   (a) preparing a solution of at least one gelatinizing agent, containing a mixture M of gelatinizing agents G1 and G2, by dissolving the said gelatinizing agents while stirring, at a temperature which is higher than the gel-sol phase transition temperature of said gelatinizing agents, in an aqueous solution;
   (b) incorporating lipids into the solution obtained in (a) while stirring the mixture, over a period of less than 5 hours; and
   (c) obtaining a dispersion of liposomes having a gelatinized internal nucleus in an aqueous phase containing the said gelatinizing agents by stirring the emulsion obtained in (b); and (2) obtaining the pulverulent product by direct drying of the resulting dispersion.

9. The process of claim 8, wherein step (2) is effected by atomization, coacervation, thin film forming or granulation.

10. A process for preparing the pulverulent composition of claim 1, in which the external matrix of the particulate units comprises a temperature-reversible aqueous gel fraction or a dextrin or both, said process, comprising:

(1) preparing a dispersion of liposomes having a gelatinized internal nucleus in aqueous phase by:
   (a) preparing a solution of at least one gelatinizing agent, containing a mixture M of gelatinizing agents G1 and G2, by dissolving the said gelatinizing agents while stirring, at a temperature which is higher than the gel-sol phase transition temperature of the said gelatinizing agents, in an aqueous solution;
   (b) incorporating lipids into the solution obtained in (a) while stirring the mixture, over a period of less than 5 hours, and
   (c) obtaining a dispersion of liposomes having a gelatinized internal nucleus in an aqueous liquid phase containing the said gelatinizing agents, by stirring the emulsion obtained in (b);

(2) at least partially removing the aqueous liquid phase which contains the said gelatinizing agents and in which the said liposomes are dispersed;

(3) adding at least one suitable dextrin; and (4) obtaining the pulverulent composition by drying, by atomization, the product obtained in (3).

11. The process of claim 10, wherein step (2) of at least partially removing the aqueous liquid phase containing the said gelatinizing agents is carried out by dilution or filtration or both.

12. The process of claim 11, wherein the aqueous solution in step (a) comprises an agent for regulating the osmolarity of the medium or a glycosidic stabilizing agent or both.

13. The process of claim 10, wherein step (b) is carried out at a shearing speed of less than 200 $s^{-1}$.

14. A method for the treatment of hypercholesterolaemias in a mammal, which comprises orally administering an effective amount of the pulverulent composition of claim 1, to a mammal in need thereof.

15. A dispersion of liposomes having gelatinized internal nuclei, as defined in claim 1, in an aqueous solution containing the mixture of gelatinizing agents as defined in claim 1, wherein the liposomes exhibit, in said dispersion, the following morphology:

a vesicular structure having a diameter of between 20 nm and 200 nm; and a polydispersity of the liposomes having a gelatinized internal phase of between 10 and 55%.

* * * * *